United States Patent
Sanabria et al.

(10) Patent No.: US 7,951,127 B2
(45) Date of Patent: May 31, 2011

(54) COMPOSITE BODYSIDE LINER

(75) Inventors: Lisa M. Sanabria, Alpharetta, GA (US); Eugenio G. Varona, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/640,110

(22) Filed: Dec. 15, 2006

(65) Prior Publication Data

US 2008/0147027 A1    Jun. 19, 2008

(51) Int. Cl.
*A61F 13/15* (2006.01)

(52) U.S. Cl. ............... 604/385.101; 604/364; 604/368; 604/374; 604/378; 604/377; 604/382

(58) Field of Classification Search ............... 604/364, 604/367–368, 374, 378–382, 385.01, 385.101
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartman |
| 3,542,615 A | 11/1970 | Dobo et al. |
| 3,692,618 A | 9/1972 | Dorschner et al. |
| 3,802,817 A | 4/1974 | Matsuki et al. |
| 3,849,247 A | 11/1974 | Richter |
| 4,340,563 A | 7/1982 | Appel et al. |
| 4,477,325 A * | 10/1984 | Osburn ................ 264/488 |
| 4,704,116 A | 11/1987 | Enloe |
| 5,192,606 A | 3/1993 | Proxmire et al. |
| 5,382,400 A | 1/1995 | Pike et al. |
| 5,486,166 A | 1/1996 | Bishop et al. |
| 5,490,846 A | 2/1996 | Ellis et al. |
| 5,514,120 A | 5/1996 | Johnston et al. |
| 5,702,377 A | 12/1997 | Collier, IV et al. |
| 5,728,081 A * | 3/1998 | Baer et al. ................ 604/370 |
| 5,763,332 A * | 6/1998 | Gordon et al. ............ 442/84 |
| 5,863,663 A * | 1/1999 | Mackey et al. ........... 428/486 |
| 5,931,823 A | 8/1999 | Stokes et al. |
| 5,948,540 A * | 9/1999 | Mackey et al. ........... 428/447 |
| 6,060,638 A | 5/2000 | Paul et al. |
| 6,149,934 A | 11/2000 | Krzysik |
| 6,150,002 A | 11/2000 | Varona |
| 6,395,955 B1 * | 5/2002 | Roe et al. ................ 604/361 |
| 6,461,716 B1 | 10/2002 | Lee et al. |
| 6,552,245 B1 | 4/2003 | Roessler et al. |
| 6,663,611 B2 | 12/2003 | Blaney et al. |
| 6,685,686 B2 | 2/2004 | Hermansson et al. |

(Continued)

FOREIGN PATENT DOCUMENTS

EP    0978584 A1    2/2000

(Continued)

*Primary Examiner* — Jacqueline F Stephens

(74) *Attorney, Agent, or Firm* — Dority & Manning, P.A.

(57) ABSTRACT

An absorbent article for fecal matter handling, especially with respect to mushy and/or pasty fecal matter, along with methods of making the same. A composite bodyside liner can reduce the amount of fecal matter that remains on the skin of a wearer after removal of the absorbent article from the wearer. The bodyside liner can include only a fluid pervious liner layer. Alternatively, the bodyside liner can include a fluid pervious liner layer and a surge layer. A fecal adhering treatment composition is applied to at least a portion of the bodyside liner to reduce the amount of fecal matter that remains on the skin of the wearer after the absorbent article is removed.

10 Claims, 5 Drawing Sheets

U.S. PATENT DOCUMENTS

| | | |
|---|---|---|
| 6,964,803 B2 | 11/2005 | Krautkramer et al. |
| 2003/0093045 A1 | 5/2003 | Erdman |
| 2003/0106605 A1 | 6/2003 | Jameson et al. |
| 2004/0009441 A1 * | 1/2004 | Ishihara et al. ............... 430/614 |
| 2004/0102750 A1 | 5/2004 | Jameson |
| 2004/0122396 A1 | 6/2004 | Maldonado et al. |
| 2004/0253894 A1 | 12/2004 | Fell et al. |
| 2005/0054255 A1 | 3/2005 | Morman et al. |
| 2005/0059941 A1 | 3/2005 | Baldwin et al. |
| 2005/0148967 A1 | 7/2005 | Baratian et al. |
| 2005/0283129 A1 | 12/2005 | Hammons |
| 2005/0288647 A1 | 12/2005 | Ellingson et al. |

FOREIGN PATENT DOCUMENTS

| | | |
|---|---|---|
| WO | WO 0117475 A1 * | 3/2001 |
| WO | WO 0234184 A1 | 5/2002 |

* cited by examiner

Figure 8: Contact Angle Frame

COMPOSITE BODYSIDE LINER

BACKGROUND

Personal care absorbent articles, such as diapers, training pants, and adult incontinence garments typically include a liquid pervious top layer (often referred to as a bodyside liner or topsheet), a liquid impermeable bottom layer (often referred to as an outer cover), and an absorbent core between them. Conventional bodyside liner materials are liquid pervious layers constructed of a nonwoven fabric such as a spunbonded layer of polypropylene spunbonded fibers. Bodyside liners are designed to provide a liquid pervious barrier between a wearer of a personal care absorbent article that includes the liner and any absorbent structures beneath the liner. The absorbent article may also include a surge layer subjacent to and in liquid communicating contact with the bodyside liner.

With this in mind, it is known to provide bodyside liners which are liquid pervious and that do not retain liquids. Such liners merely act as a pass through or separation layer. The structure of such bodyside liners is optimized primarily based on providing liquid intake and dryness, mostly with respect to urine.

In addition to urine, absorbent articles are also subjected to insults of runny, mushy, and/or pasty fecal matter. Although efforts have been made to absorb, contain, or otherwise entrap runny fecal matter, conventional bodyside liners do not provide sufficient intake of runny fecal matter and do not sufficiently limit the spread of runny fecal matter. Consequently, runny fecal matter has a greater tendency to spread and leak, than does urine, from some conventional absorbent articles. Additionally, the fecal matter has a tendency to stick to the skin of the wearer, requiring a caretaker to thoroughly wipe the skin area clean, even after removal of the absorbent article.

Accordingly, there exists a need to provide a composite liner that provides improved intake of fecal material. Further, there exists a need to minimize the amount of fecal material remaining on the skin of the wearer once a disposable absorbent article is removed.

SUMMARY

In accordance with one embodiment of the present invention, an absorbent article comprising an outer cover, an absorbent core, and a composite bodyside liner is generally disclosed. The composite bodyside liner can comprise a surge layer and a liquid pervious liner material defining an outer surface. The outer surface of the liquid pervious liner material can define an outermost surface of the absorbent article, and the surge layer is positioned between the liquid pervious liner material and the absorbent core. A fecal adhering treatment composition is applied to at least a portion of the surge layer. The fecal adhering treatment composition can comprises a polar component, which is present on the surge layer at an add-on level of at least about 1% by weight of the surge layer, such as at least about 2% by weight, or from about 5% by weight to about 25% by weight. The polar component can be cationic (such as a cationic polymer-epichlorohydrin adduct), anionic, or amphoteric.

In one particular embodiment, the fecal adhering treatment composition can impart a contact angle of fecal fluid extract of less than about 90° on the surge layer, such as less than about 75°, or from about 10° to about 60°. Also, the fecal adhering treatment composition can impart a surface tension of at least about 20 dynes/cm on the surge layer at room temperature, such as greater than about 30 dynes/cm, or from about 35 dynes/cm to about 40 dynes/cm.

In one embodiment, the composite bodyside liner can be a topographical composite bodyside liner including a liquid pervious liner material, a topographical surge layer, and a fecal adhering treatment composition. The topographical surge layer defines peaks and valleys in at least one surface to provide topography to the composite topographical bodyside liner. As such, the fecal adhering treatment composition can be applied only to the valleys defined by the topographical surge layer. Additionally, or in the alternative, an anti-adherent fecal treatment composition can be applied only to the peaks defined by the topographical surge layer. Also, a skin beneficial agent can be applied to the peaks defined by the topographical surge layer.

Other features and aspects of the present invention are discussed in greater detail below.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
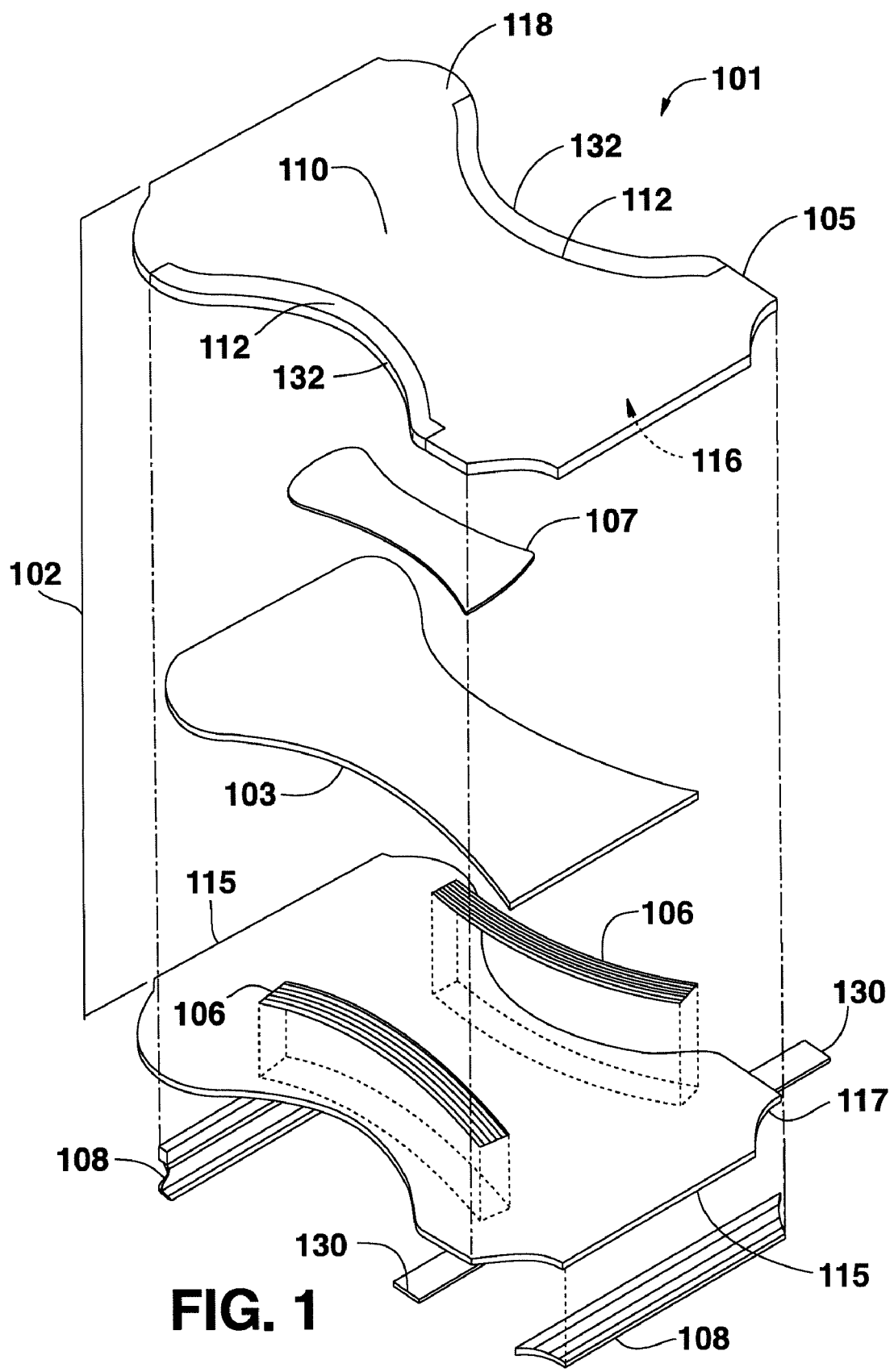
FIG. 1 is a perspective view of an exemplary absorbent article that may be formed according to one embodiment of the present invention.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Definitions

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous filaments. The filaments are formed by extruding a molten thermoplastic material from a plurality of fine, usually circular, capillaries of a spinnerette with the diameter of the extruded filaments then being rapidly reduced as by, for example, eductive drawing and/or other well-known spunbonding mechanisms. The production of spunbond webs is described and illustrated, for example, in U.S. Pat. No. 4,340,563 to Appel, et al., U.S.Pat. No. 3,692,618 to Dorschner, et al., U.S. Pat. No. 3,802,817 to Matsuki, et al., U.S. Pat. No. 3,338,992 to Kinney, U.S Pat. No. 3,341,394 to Kinney, U.S. Pat. No. 3,502,763 to Hartman, U.S. Pat. No. 3,502,538 to Petersen, U.S. Pat. No. 3,542,615 to Dobo, et al., and U.S. Pat. No. 5,382,400 to Pike, et al., which are incorporated herein in their entirety by reference thereto for all purposes. Spunbond filaments are generally not tacky when they are deposited onto a collecting surface. Spunbond filaments may sometimes have diameters less than about 40 micrometers, and are often between about 5 to about 20 micrometers.

As used herein, the term "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

DETAILED DESCRIPTION

The present invention is generally directed to an absorbent article having improved fecal matter handling, especially with respect to mushy and/or pasty fecal matter, and methods of making the same. For example, an absorbent article can have a composite bodyside liner that reduces the amount of fecal matter that remains on the skin of a wearer after removal of the absorbent article from the wearer.

The bodyside liner is generally constructed of one or more layers. For instance, in one embodiment, the bodyside liner can include only a fluid pervious liner layer. In another embodiment, the bodyside liner can be constructed of at least two layers, including a fluid pervious liner layer and a surge layer. According to the present invention, a fecal adhering treatment composition is applied to at least a portion of the bodyside liner, such as to the fluid pervious liner layer, to form a composite bodyside liner. The fecal adhering treatment composition can be uniformly or non-uniformly applied to the composite bodyside liner. For instance, the fecal adhering treatment composition can be uniformly or non-uniformly applied to the fluid pervious liner layer. Alternatively, or in addition to, the fecal adhering treatment composition can be applied to the surge layer, when present in the bodyside liner, either uniformly or non-uniformly.

The application of a fecal adhering treatment composition to the bodyside liner can reduce the amount of fecal matter that remains on the skin of the wearer after the absorbent article is removed. For example, when the composite bodyside liner is removed from contact with the skin of the wearer, the fecal adhering composition helps retain fecal matter in and on the absorbent article, effectively reducing the amount of fecal matter left on the skin, when compared to an absorbent article without any fecal matter treatment composition applied to a composite bodyside liner.

For instance, an absorbent article having at least a portion of its bodyside liner treated with a fecal adhering treatment composition can retain greater than about 40% by weight of fecal matter after being soiled by a. user, such as greater than about 50% by weight. For instance, an absorbent article having at least a portion of its bodyside liner treated with a fecal adhering treatment composition can retain greater than about 60% by weight of fecal matter after being soiled by a user, such as from about 65% by weight to about 90% by weight.

A. Fecal Adhering Treatment Composition

Any suitable composition can be used as the fecal adhering treatment composition, provided that the application of the composition to the bodyside liner increases the ability of the formed composite bodyside liner to adhere to fecal matter. For example, in one embodiment, the fecal adhering treatment composition can include a polar component. The polar component can be cationic, amphoteric, or anionic. For example, the polar component can have a surface tension of no less than about 2 dynes/cm, such as no less than 2.13 dynes/cm, at room temperature (e.g., about 20° C. to about 25° C.). For instance, the polar component, in some embodiments, may have a surface tension at room temperature of greater than about 5 dynes/cm, such as from about 10 dynes/cm to about 100 dynes/cm, and from about 30 dynes/cm to about 90 dynes/cm.

The polar component of the fecal adhering treatment composition can provide the treated surface of the composite bodyside liner with a surface tension of greater than about 20 dynes/cm, such as no less than 30 dynes/cm, at room temperature. For example, the treated surface of the composite bodyside, in some embodiments, may have a surface tension at room temperature of greater than about 35 dynes/cm, such as from about 35 dynes/cm to about 50 dynes/cm, from about 35 dynes/cm to about 50 dynes/cm, and from about 37 dynes/cm to about 40 dynes/cm.

Without wishing to be bound by theory, it is believed that a polar component can attract the particles in the fecal matter since those particles are typically charged. More specifically the fluid in fecal matter has a highly polar component to its surface tension as opposed to a more dispersive component. Fecal matter, especially mushy/pasty fecal matter, is typically a highly polar fluid having particles dispersed throughout. For example, as discussed in the Examples of the present application, fecal fluid extract from a slurry of human fecal matter has a surface tension of about 37.5 dynes/cm. More specifically, the extract from the human fecal matter has a polar component of about 25.5 dynes/cm and a dispersive component of about 12.0 dynes/cm. As such, it is believed that a polar component applied to the composite bodyside liner can attract and retain, through polar forces such as ionic bonding, hydrogen bonding, van der Waals forces, etc., fecal matter on the liner due to its highly polar component in the surface tension of the fecal matter. Thus, the amount of fecal matter retained in and on the absorbent article can be increased, while reducing the amount of fecal matter that remains on the skin of the wearer, when compared to a conventional absorbent article without any fecal adhering treatment composition.

Additionally, it is believed that in a high humidity environment, such as found within a soiled absorbent article, water can condensate on the top layer, thus blocking some of the effect of a fecal adherent treatment on the bodyside liner; however, the fecal matter can make contact with a polar component found, for instance, on the underlying surge layer.

In one embodiment, the fecal adhering treatment composition can impart a contact angle for fecal fluid extract of 90° or less to the composite bodyside liner, such as less than about 80° or less than about 75°. For example, the fecal adhering treatment composition can impart a contact angle for fecal fluid extract of from about 0° to about 60°, such as from about 10° to about 50°, and from about 20° to about 45°. As used herein, "contact angle" refers to the angle at which a liquid (e.g., fecal fluid extract) interface meets a surface (e.g., a composite bodyside liner). The contact angle of fecal fluid extract can be calculated according to the method described below in the Examples section of the present application.

In one embodiment, the polar component may be cationic. Suitable cationic polar components include, but are not limited to, cationic polymer-epichlorohydrin adducts, chitosan, polyhexamethylene biguanide, quaternary ammonium halides, and other highly cationic polymers. For example, in one embodiment, the polar component can include a cationic polymer-epichlorohydrin adduct, such as polyamide (polyamide-polyamine) epichlorohydrin adducts, polyamine epichlorohydrin adducts, and amine polymer epichlorohydrin adducts. Polyamide-epichlorohydrin adducts are prepared by reacting epichlorohydrin with the polycondensation product of a polyalkylene polyamine with a polycarboxylic acid such as diethylene triamine with a dibasic acid such as adipic acid. Polyamine epichlorohydrin adducts are made by condensing a polyalkylene polyamine directly with epichlorohydrin. These adducts include polyalkylene polyamines which are linked together with dihalides to form higher polyamines before reacting them with epichlorohydrin. Amine polymer epichlorohydrin adducts include resins in which the monomeric amine is polymerized to a polyamine precursor which is then alkylated and reacted with epichlorohydrin. They include amines substituted polymers of vinyl, allyl, acrylate or epoxy monomers. The epichlorohydrin adducts whether the polymer is a polyamide, a polyamine or an amine polymer react with the epichlorohydrin by different routes. If the amino group in the polymer chain is a primary amine, two epichlorohydrin molecules reacted with the nitrogen and form a disubstituted chlorohydroxypropyl substituted amine group. Secondary amine groups react with epichlorohydrin to form a tertiary aminochlorohydrin group which cyclizes to form a reactive 3-hydroxyazetidinium salt moiety. Tertiary amine groups react with epichlorohydrin to form a glycidyl; (2,3 epoxypropyl) ammonium salt.

In a particular embodiment, the epichlorohydrin adducts have an average molecular weight of less than about 150,000 g/mol. Also, in one embodiment, at least 50 mole percent of the functional groups in the adduct are the azetidinium group. A preferred polymer is one in which about 90% of the substitution is in the form of an azetidinium group and about 10% as an epoxide group.

Exemplary epichlorohydrin adduct products are Reten® 204LS and Kymeme® 557LX; available from Hercules Inc., Wilmington, Del. These products are sold as an aqueous solution of the reactive epichlorohydrin adduct. For instance, the Reten® 204LS product is available as a 15% aqueous solution.

When used, the cationic polymer-epichlorohydrin adduct can be applied to the topographical surge layer at an add-on level of at least about 1% by weight of the surge layer, such as at least about 2% by weight. For example, in one particular embodiment, the cationic polymer-epichlorohydrin adduct can be applied to the topographical surge layer at an add-on level of from about 5% by weight to about 25% by weight, such as from about 5% by weight to about 20% by weight.

In another embodiment, the polar component can be a cationic compound used in the past as antimicrobial components, such as quaternary ammonium halide compounds and cationic polymers. For example, cationic quaternary ammonium halide compounds can include, but are not limited to, 3-(trimethyloxysilyl)propyloctadecyl ammonium chloride, alkyl dimethyl benzyl ammonium chloride, alkyl dimethyl ethylbenzyl ammonium chloride, and the like. Other suitable cationic components or cationic polymers can include, but are not limited to, polyhexamethylene biquanide, amino polysaccharides, silicon quaternary ammonium compounds, 2-acylamido-2-methyl-1-propanesulfonic acid, methylbenzethonium chloride, polydimethyldiallyl ammonium chloride, cetyl pyridium chloride, cetyl trimethyl ammonium chloride, cetrimonium bromide, stearalkonium chloride, polyethylene imine, quaternary nitrogen, and urea-formaldeyde.

In other embodiments, the highly polar compound can be anionic, such as colloidal silica in solution. Other suitable anionic compounds include, but are not limited to, partially neutralized acrylic acid based polymers and copolymers, such as sulfonated polyester polymers, and other anionic synthetic polymers, such as polyacrylamides, carboxymethylcellulose, and glyoxylated polyacrylamide.

In yet other embodiments, the highly polar compound can be amphoteric, such as polyacrylamidomethylpropane sulfonic acid, aluminum hydroxide, amino acids, hydrogen carbonate, hydrogen sulfonate, proteins, and the like.

In one embodiment, less than about 1% by weight of a surfactant is present in the fecal adhering treatment composition. For example, the fecal adhering treatment composition can have no appreciable amount of a surfactant present, such as no surfactant. As known in the art, surfactants can lower the surface tension of a liquid. As such, if a surfactant is present in the fecal adhering treatment composition, the surface tension of the composite bodyside liner may be lowered, which can cause the contact angle of fecal fluid extract to increase. Thus, the presence of a surfactant in the fecal adhering treatment composition may, in some embodiments, adversely affect the ability of the composite bodyside liner to retain fecal matter.

Alternatively, the contact angle of fecal fluid extract can be controlled by the addition of a surfactant to the fecal adhering treatment composition. The surfactant can lower the surface tension of the fecal fluid extract to a desired value, effectively controlling the contact angle of the fecal fluid extract on the composite bodyside liner. Thus, one of ordinary skill in the art can somewhat control the interaction of the composite bodyside liner and fecal matter.

B. Bodyside Liner Topography

In one particular embodiment, the topography can be imparted on at least one surface of the bodyside liner forming a topographical bodyside liner. The terms "topography" and "topographical" refer to a surface that does not exist in a single plane, but rather contains portions that are either raised or lowered. Thus, as a result of the topography of the bodyside liner, the bodyside liner has peaks (e.g., raised areas) and valleys (e.g., depressed areas) situated in the z-direction of at least one surface of the bodyside liner.

For example, the fluid pervious liner layer can be a topographical fluid pervious liner layer. Thus, the topographical fluid pervious liner layer has peaks and valleys along at least one surface. As a result of the topography of the fluid pervious liner layer, fecal matter can be held and trapped within the valleys of the topography. Alternatively, the surge layer, when present in the bodyside liner, can be a topographical surge layer.

In one particular embodiment, the fecal adhering treatment composition can be applied only to the valleys of a topographical bodyside liner, such as to the valleys of a topographical fluid pervious liner layer. The application of the fecal adhering treatment composition to the valleys of the bodyside liner can allow the fecal matter to migrate to those valley areas. Thus, the amount of fecal matter located on the peaks of the composite bodyside layer, which contacts the skin of the wearer, can be reduced. Also, when the absorbent article is removed from the wearer, the fecal adhering treatment composition can retain more of the fecal matter in or on the absorbent article, effectively reducing the amount of fecal matter remaining on the skin of the wearer.

In the embodiment where the fecal adhering treatment composition is applied to the valleys of the topography of the bodyside liner, an anti-adherent fecal treatment composition can be added to the peaks of the topographical composite bodyside liner. Thus, the addition of the anti-adherent fecal treatment can wick fecal matter off the peaks of the composite bodyside liner and into the valleys, helping to minimize the contact of fecal matter and the skin of the wearer. The anti-adherent fecal treatment composition can impart a relatively low surface tension to the peaks of the topographical composite bodyside liner, such as less than about 10 dynes/cm. For example, the anti-adherent fecal treatment composition can impart a surface tension to the peaks of the topographical composite bodyside liner of less than about 5 dynes/cm, such as less than about 2 dynes/cm. Also, the anti-adherent fecal treatment composition can impart a contact angle of fecal fluid extract of greater than 90°, such as greater than about 100°.

In other embodiments, a skin beneficial agent can be added to the peaks of the topographical composite bodyside liner. The skin beneficial agent can be added to the peaks with or without an anti-adherent fecal treatment composition. Possible beneficial agents that may be applied to the peaks include, without limitation, antimicrobial actives, antifungal actives, antiseptic actives, antioxidants, cosmetic astringents, drug astringents, biological additives, deodorants, emollients, external analgesics, film formers, fragrances, humectants, natural moisturizing agents and other skin moisturizing ingredients known in the art such as lanolin, opacifiers, skin conditioning agents, skin exfoliating agents, skin protectants, solvents, sunscreens, and surfactants. More specifically, vitamin E and aloe vera extracts are examples of beneficial agents which may be applied to a surface of a web according to the present inventive process.

The topography may be imparted to the topographical bodyside liner in numerous ways. For example, the sheet(s) that forms the topographical bodyside liner may be formed on a surface that includes topographical features. The sheet may then be bonded such as with hot air to provide a fabric with surface features. Alternatively, the sheet that forms the topographical bodyside liner may be creped or otherwise mechanically strained to provide topographical features. The sheet may also be patterned bonded thereby providing higher and lower densities in the web which may impart a topography to the sheet. The sheet could also be embossed to impart the topography. The topographical bodyside liner may be formed by a differential basis weight. For example, this differential basis weight may be accomplished by either adding or removing material from the sheet either before or after the sheet is bonded into a fabric. No matter the method of providing topography to the bodyside liner, the topographical bodyside liner can take on any 3-dimensional shape.

Figure 2:
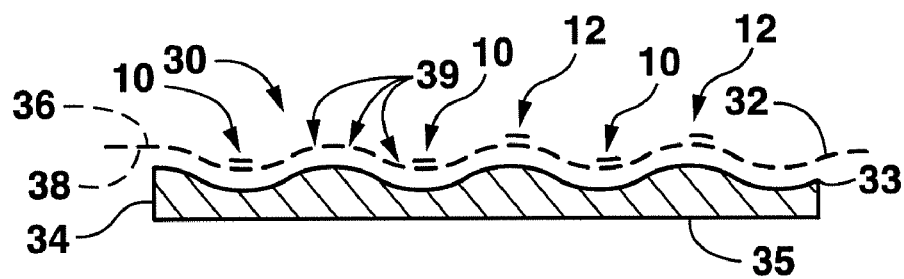
FIGS. 2-3 illustrate cross-sectional views of exemplary configurations of a topographical composite bodyside liner.

In one embodiment, a topographical surge layer can be present in the topographical bodyside liner. The topography of the surge layer can impart a topography to the bodyside liner. For example, as illustrated in FIGS. 2-7, the bodyfacing surface 33 of the topographical surge layer 34 may take on numerous surface topographies. Additionally, the lower surface 35 of the topographical surge layer 34 may take on numerous surface topographies. FIG. 2 illustrates a liner composite 30 with a topographical surge layer 34 that has a generally flat lower surface 35 and a topographical bodyfacing surface 33. Specifically the bodyfacing surface 33 has a topography similar to that of a sine wave with generally uniform amplitude and wavelength. This surface topography may exist in only the lateral or longitudinal direction of the topographical surge layer 34 in which case the surface topography may resemble corrugations. This surface topography may exist in both the lateral and longitudinal direction of the topographical surge layer 34 in which case the surface topography may resemble a quilted pattern.

As shown in the exemplary embodiment of FIG. 2, a fecal adhering treatment composition 10 can be applied to the valleys of the topographical bodyside liner, such as to the valleys of a topographical fluid pervious liner layer 32. Additionally, a skin beneficial agent 12 can be applied to the peaks defined by said topographical composite bodyside liner, such as to the peaks of the topographical fluid pervious liner layer 32.

Figure 3:
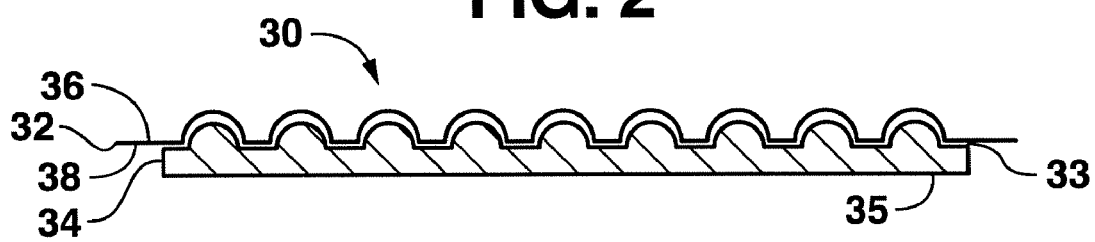
Figure 4:
FIGS. 4-7 illustrate cross-sectional views of exemplary configurations of a topographical surge layer.

FIG. 3 illustrates another topographical surge layer 34 that has a generally flat lower surface 35 and a topographical bodyfacing surface 33. Specifically the bodyfacing surface 33 has a topography which resembles a flat surface with semi circles protruding upwards from the flat surface. The semi circles are of uniform size, shape and spacing. Alternatively, the size, shape and spacing may be non-uniform. FIG. 4 illustrates another topographical surge layer 34 that has a generally flat lower surface 35 and a topographical bodyfacing surface 33. Specifically the bodyfacing surface 33 has a topography which resembles a flat surface with semi circles protruding downward into the flat surface. The semi circles are of uniform size, shape and spacing. Alternatively, as described above, the size, shape and spacing may be non-uniform.

Figure 5:
Figure 6:
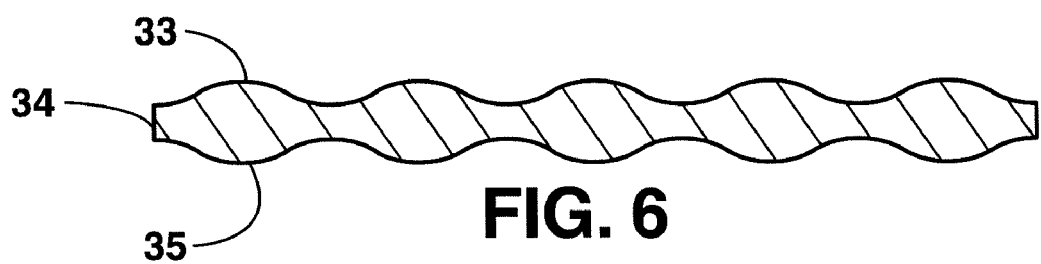

FIG. 5 illustrates a topographical surge layer 34 that has a topographical lower surface 35 and a topographical bodyfacing surface 33. Specifically both the bodyfacing surface 33 and the lower surface 35 have a topography that resembles sine waves. More specifically, the sine waves of the bodyfacing surface 33 and the lower surface 35 are in phase such that the thickness along the length of the topographical surge layer 34 generally is uniform. FIG. 6 illustrates a topographical surge layer 34 that has a topographical lower surface 35 and a topographical bodyfacing surface 33. Specifically both the bodyfacing surface 33 and the lower surface 35 have a topography that resembles a sine wave. More specifically, the sine waves of the bodyfacing surface 33 and the lower surface 35 are 180 degrees out of phase such that the thickness along the length of the topographical surge layer 34 is at a maximum when the surface of the bodyfacing surface 33 is at a peak, and the thickness of the topographical surge layer 34 is at a minimum when bodyfacing surface is at a trough.

Figure 7:

FIG. 7 illustrates another topographical surge layer 34. Specifically the bodyfacing surface 33 has a topography similar to that of a sign wave with uniform amplitude; however, the wavelength varies from longer wavelengths to shorter wavelengths. Additionally, the amplitude may vary, for example in a pattern of low, high, low, high, etc. or in a pattern from a minimum to a maximum and then back to a minimum.

These examples illustrate how surface features of the topographical surge layer may be combined and modified. Additionally, while the surface features have been described as viewed from a cross sectional perspective, one skilled in the art will recognize that in a given topographical surge layer the topographical features may differ when comparing the pattern in a longitudinal direction versus the pattern in a lateral direction. For example, the amplitude of the topographical features may be uniform in a longitudinal direction, but may vary in a lateral direction. Other examples of suitable topographical surge layers are disclosed in U.S. Publication No. 2005/0288647 of Ellingson, et al., which is incorporated by reference.

Various woven and nonwoven fabrics can be used to construct the topographical surge layer. Typically, the surge layer is constructed from highly liquid-permeable materials. Suitable materials may include porous woven materials, porous nonwoven materials, and apertured films. In one particular embodiment, the surge layer includes a nonwoven web. For example, the topographical surge layer may be a layer composed of a meltblown or spunbond web of synthetic fibers, such as polyolefin fibers. The topographical surge layer may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The topographical surge layer may be composed of a substantially hydrophobic material, and the hydrophobic material may optionally be treated with a surfactant or otherwise processed to impart a desired level of wettability and hydrophilicity. Particular embodiments of the topographical surge includes a hydrophobic, fibrous nonwoven material having a basis weight of greater than about 30 gsm, alternatively, greater than about 50 gsm, and finally, alternatively, greater than about 70 gsm. Another embodiment of the topographical surge layer includes a nonwoven, bonded-carded-web comprising polyethylene/polyester bicomponent fibers, the web having a basis weight within the range of about 17-102 gsm and a density within the range of about 0.02-1.0 gm/cc, and the fibers having a size within the range of 0.9-18 denier.

Desirably, a surge material can rapidly accept and temporarily hold the liquid prior to releasing the liquid into the storage or retention portions of the absorbent structure. Examples of suitable surge materials are described in U.S. Pat. No. 5,486,166 issued to Bishop. et al., and U.S. Pat. No. 5,490,846, issued to Ellis et al., the entire disclosures of which are hereby incorporated by reference in a manner that is consistent herewith.

In one particular embodiment, the topographical surge layer can be an apertured nonwoven web, such as an apertured spunbond web. The spunbond web can be constructed from, for instance, continuous filaments made from polypropylene fibers. For instance, in one particular embodiment, the topographical surge layer can be an apertured, creped spunbond web. In this particular embodiment, the creping provides topography to the surge layer.

In other embodiments, the topographical surge layer can be a relatively thin cellulose paper sheet. The cellulose paper sheet can, in one embodiment, be apertured to have pore sizes of a desired size and shape.

In one particular embodiment, the topographical surge layer can have its own ion exchange capacity. For example, the topographical surge layer can have an ion exchange capacity of at least about 1.5 µeq/cm$^2$.

Also, the topographical surge layer can typically be less hydrophilic than the absorbent core which it may be associated with, and has an operable level of density and basis weight to quickly collect and temporarily hold liquid surges, to transport the liquid from its initial entrance point and to substantially completely release the liquid to other parts of the absorbent core. This configuration can help prevent the liquid from pooling and collecting on the portion of the fluid pervious liner layer positioned against the wearer's skin, thereby reducing the feeling of wetness by the wearer. The structure of the topographical surge layer also generally enhances the air exchange within an absorbent article.

The surge layer can help to decelerate and diffuse surges or gushes of liquid that may be rapidly introduced into the absorbent core. Desirably, the surge layer rapidly accepts and temporarily holds the liquid prior to releasing it into the storage or retention portions of the absorbent core. In most embodiments, the surge layer is interposed between an inwardly facing surface of the bodyside liner and the absorbent core. Alternatively, the surge layer may be located on an outwardly facing surface of the bodyside liner.

C. Fluid Pervious Liner Layer

As discussed above, the fluid pervious liner layer can be used alone or in combination with other layers, such as a surge layer, to form the bodyside liner. When incorporated into a disposable absorbent article, the fluid pervious liner layer can be in close proximity to the skin of the wearer, often it is the outermost layer contacting the skin of the wearer. Consequently, the liner material is desirably as compliant, soft feeling, and non-irritating to the wearer's skin as possible.

In one particular embodiment, when a surge layer is present in the bodyside liner, the fluid pervious liner layer and the surge layer can be selected to create a capillary gradient between the fluid pervious liner layer and the surge layer. In one embodiment, the fluid pervious liner layer can have a fairly low capillary tension compared to the underlying treated surge layer. Specifically, when subtracting the capillary tension of the underlying treated surge layer from the overlying fluid pervious liner layer, a difference of at least about 2.5 cm of fecal fluid extract can exist, such as at least about 5 cm of fecal fluid extract. As such, fecal fluid extract will tend to migrate away from the overlying fluid pervious liner layer and to the underlying surge layer. Thus, the fecal fluid extract can be wicked away from contact with the skin of the wearer. Such a capillary gradient can be created, for example, by treating the surge layer with a fecal adhering treatment composition.

The fluid pervious liner layer can have an appropriate amount of flexibility, or drape, such that the when a fluid pervious liner layer and a topographical surge layer come together to form a bodyside liner, the topography of the topographical surge layer is at least partially imparted on the bodyfacing surface of the fluid pervious liner layer.

For instance, as illustrated in FIGS. 2 and 3, the composite bodyside liner 30 includes a sheet of fluid pervious liner layer 32 and a topographical surge layer 34. The fluid pervious liner layer 32 has a bodyfacing or upper surface 36 and an opposing or lower surface 38. The topographical surge layer 34 has a bodyfacing or upper surface 33 and an opposing or lower surface 35. The fluid pervious liner layer 32 and the topographical surge layer 34 are in liquid communication with one another. As used herein when describing the fluid pervious liner layer 32 in a relation to the topographical surge layer 34 and vice versa, the term "liquid communication" means that liquid is able to travel from one layer to another layer or one location to another location. The fluid pervious liner layer 32 may be attached, either directly or indirectly, to the topographical surge layer 34 by any suitable method, such as by adhesive, cohesive, pressure, thermal bonds, ultrasonic bonds, and the like.

As shown in FIG. 2, the topographical surge layer 34 imparts its shape on the bodyfacing surface 36 of the fluid pervious liner layer 23. Alternatively, as illustrated in FIG. 3, the topographical surge layer 34 may contain surface features that are not completely imparted on the bodyfacing surface 36 of the fluid pervious liner layer 32. The drapability of the fluid pervious liner layer 32 and the size and shape of the surface features of the topographical surge layer 34 may be such that the fluid pervious liner layer 32 does not contour to each and every aspect of the surface features of the topographical surge layer 34, therefore only a portion of the topographical features of the topographical surge layer 34 are imparted on the bodyfacing surface 36 of the fluid pervious liner layer 32. The resulting liner composite 30 therefore has pockets that exist between the fluid pervious liner layer 32 and the topographical surge layer 34. These pockets may provide for storage and distribution of insulting exudates while providing separation from the skin of the wearer.

Providing the surface of the liner composite 30 and the topography of the surface of the liner composite 30 with separate materials provides unique benefits. For example, a first material may have a high degree of resiliency, but may be undesirable for skin contact. This first material may form the topographical surge layer 34 while a soft, skin friendly material, which may have very little resiliency, may form the fluid pervious liner layer 32. Secondly, in many applications the topography is desired in one area of the liner composite 30 and not in another. For example, the topography may be desired in the area of the liner composite 30 which is likely to receive an insult, while for cost, aesthetics, or functional reasons, no topography may be desired in the rest of the liner composite 30. Additionally, for aesthetic and manufacturing purposes, a uniform liner is desired. The liner composite 30 makes it possible to satisfy these two desires. Further, the liner composite 30 may contain a first topographical surge layer 34 and a second surge layer (not shown), the first topographical surge layer 34 may be designed for accepting feces and located accordingly, while the second surge layer may be designed for accepting urine and also located accordingly. The first and second topographical surge layers may have similar topographies, or alternatively, the first and second topographical surge layers may have dissimilar topographies. Further, the liner composite 30 may contain a first topographical surge layer 34 and a second surge layer which does not have any surface topography. Further still, the two surge materials may differ in basis weight, density or composition.

The topographical features of the liner composite 30 are desirably resilient and can minimize contact of a wearer's skin with the fluid pervious liner layer 32. It is believed that the "land" areas or recesses between topographical features allow for mushy/pasty bowel movement to reside in these lower areas and away from a wearer's skin. The topographical features may also deter the movement of feces across the bodyfacing surface 36 of the fluid pervious liner layer 32 thus minimizing the spread of fecal matter. This is advantageous because it may provide for a smaller spreading pattern and minimize the contact area of the fecal matter with the skin of a wearer of the absorbent article. Desirably, the bodyfacing surface 36 of the liner composite 30 has projections and optional depressions or other structures that are compressible and return to the original shapes to provide separation between a wearer and the liner composite 30.

In one embodiment, the liner material may be apertured. For instance, as shown in FIG. 2, the fluid pervious liner layer 32 may include apertures 39. The apertures 39 may be randomly or uniformly arranged through the fluid pervious liner layer 32. Alternatively, the apertures 39 can be selectively confined to certain areas of the fluid pervious liner layer 32, e.g., located in a narrow longitudinal band or strip within the fluid pervious liner layer 32. The size, shape and number of apertures 39 can be varied depending on the desired application. The apertures 39 may be formed in the fluid pervious liner layer 32 by any suitable method, for example, by pin aperturing, laser perforation, hydraulic rearrangement, slitting and stretching of the polymeric film, or vacuum aperturing, wherein the resulting apertured cover has an open area and a plurality of protuberances. The protuberances may have a tapered profile.

The number of apertures 39 per square inch may range from about 6 apertures/in$^2$ (1 aperture/cm$^2$) to about 1100 apertures/in$^2$ (170 apertures/cm$^2$) and preferably ranges from about 50 apertures/in$^2$ (8 apertures/cm$^2$) to about 300 apertures/in$^2$ (46 apertures/cm$^2$). The apertures may be circular in shape; alternatively, the apertures may be oval in shape or any other shape.

When utilized, the size of the apertures in the liquid pervious liner can be selected to help trap fecal mater particles in or within the liner. For example, the dimensions of the apertures may be uniform, all the apertures having the same size; or alternatively, the apertures may have sizes that vary from one aperture to another, or one set of apertures to another set of apertures. Desirably the apertures have one dimension that is greater than about 0.1 mm, such as from about 0.25 mm to about 0.5 mm, although the approximate dimension may vary according to, inter alia, the general design and intended use of the liner composite 30.

The apertures may be uniformly, non-uniformly or randomly disposed over the full surface of over a portion of the fluid pervious liner layer 32. In particular embodiments, the apertures are disposed in a predetermined portion of the fluid pervious liner layer 32 which may define a rectangular or oblong area and may be centrally located on the surface of the fluid pervious liner layer 32. Alternatively, the apertures may cover the entire area of the fluid pervious liner layer 32. The apertures in the fluid pervious liner layer 32 may coincide with a portion of the liner that overlays the topographical surge layer 34. The apertures may allow a fluid impinging upon the outer surface of the fluid pervious liner layer 32 to be quickly transferred through the fluid pervious liner layer 32.

In one embodiment, the apertured liner can be formed to have a bimodal pore size distribution. Generally speaking, a bimodal pore size distribution describes a structure that has at least two distinct classes of pores (without considering the micropores within the fibers themselves). For example, the bimodal pore size distribution may describe a first class of larger pores formed by the apertures and a second class of pores that are smaller and defined between neighboring fibers. In other words, the distribution of fibers in the fibrous structure is not uniform throughout the space of the material, such that distinct cells having no or relatively few fibers can be defined in distinction to the pore spaces between neighboring or touching fibers. For example, the larger pores formed by the apertures of the web can have a diameter or width of from about 200 to about 2000 microns, and in some embodiments, from about 250 to about 500 microns. On the other hand, the smaller pores formed by the non-apertured spaces of the web can have a diameter or width of from about 20 to about 200 microns, and in some embodiments, from about 20 to about 140 microns. A bimodal pore size distribution can result in enhanced absorption properties of fecal matter. Specifically, the larger pores are generally better for handling particles and oils, while the smaller pores are generally better for handling aqueous liquids. Further, the presence of larger pores also allows the resulting fabric to remain relatively stretchable in comparison to fabrics containing only small pores. Likewise, the surge layer may also have a bimodal pore size distribution.

Alternatively, the fluid pervious liner layer 32 may be coapertured with the topographical surge layer 34 or any other material. The term "coapertured" refers to a composite wherein at least two materials are apertured together to create holes which extend through the layers.

A suitable fluid pervious liner layer 32 may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims. Suitable woven and nonwoven materials can include natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers), or a combination of natural and synthetic fibers. When the fluid pervious liner layer 32 includes a nonwoven web, the web may be spunbond, carded, wet-laid, meltblown, hydroentangled, combinations of the above, or the like. The fluid pervious liner layer 32 is suitably employed to help isolate the wearer's skin from liquids. The fluid pervious liner layer 32 can also be made from extensible materials as are described in U.S. Pat. No. 6,552,245 issued on Apr. 22, 2003 to Roessler et al. The fluid pervious liner layer 32 can also be made from biaxially stretchable materials as are described in WO 02/34184 filed on Oct. 27, 2000 by Vukos et al. the entire disclosure of which is hereby incorporated by reference in a manner that is consistent herewith.

The fluid pervious liner layer 32 may be composed of a substantially hydrophobic material, and the hydrophobic material may optionally be treated with a surfactant or otherwise processed to impart a desired level of wettability and hydrophilicity. In a particular embodiment of the present invention, the fluid pervious liner layer 32 is made from a nonwoven, spunbond, polypropylene fabric composed of fibers having a fiber diameter of about 21 to 23 microns formed into a web having a basis weight of about 20 grams per square meter and a density of about 0.13 grams per cubic centimeter. The fabric may be surface treated with about 0.3 weight percent of a surfactant, such as a surfactant commercially available from Hodgson Textile Chemicals, Inc. under the trade designation AHCOVEL Base N-62. The surfactant may be applied by any conventional means, such as spraying, printing, foaming, brush coating or similar techniques. The surfactant may be applied to the entire fluid pervious liner layer 32 or may be selectively applied to particular sections of the fluid pervious liner layer 32, such as the medial section, to provide greater wettability of such sections. The fluid pervious liner layer 32 may further include a lotion or treatment applied thereto that is configured to be transferred to the wearer's skin. Suitable compositions for application to the fluid pervious liner layer 32 are described in U.S. Pat. No. 6,149,934 that issued to Krzysik et al. on Nov. 21, 2000.

Desirably the caliper of the fluid pervious liner layer 32 is less than about 6 mm, alternatively, less than about 4 mm, and finally, alternatively, less than about 2 mm; although the approximate caliper may vary according to, inter alia, the general design and intended use of the fluid pervious liner layer 32.

In the embodiment without a surge layer present, the fluid pervious liner layer may have a topography imparted by any means, such as those discussed above with reference to the surge layer. Also, a topographical fluid pervious liner layer may have any topography defining peaks and valleys, such as described above with reference to the surge layer.

D. Absorbent Articles

Various embodiments of an absorbent article that may be formed according to the present invention will now be described in more detail. For purposes of illustration only, an absorbent article is shown in FIG. 1 as a diaper 101. However, as noted above, the invention may be embodied in other types of absorbent articles, such as incontinence articles, sanitary napkins, diaper pants, feminine napkins, children's training pants, and so forth. In the illustrated embodiment, the diaper 101 is shown as having an hourglass shape in an unfastened configuration. However, other shapes may of course be utilized, such as a generally rectangular shape, T-shape, or I-shape. As shown, the diaper 101 includes a chassis 102 formed by various components, including an outer cover 117, bodyside liner 105, absorbent core 103, and surge layer 107. It should be understood, however, that other layers may also be used in the present invention. Likewise, one or more of the layers referred to in FIG. 1 may also be eliminated in certain embodiments of the present invention.

The outer cover 117 is typically formed from a material that is substantially impermeable to liquids. For example, the outer cover 117 may be formed from a thin plastic film or other flexible liquid-impermeable material. In one embodiment, the outer cover 117 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 may be formed from a polyolefin film laminated to a nonwoven web. For example, a stretch-thinned polypropylene film having a thickness of about 0.015 millimeter may be thermally laminated to a spunbond web of polypropylene filaments. If desired, the nonwoven web of the present invention may be used to form the outer cover 117.

The diaper 101 also includes a bodyside liner 105. The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. The liner 105 may be liquid-permeable to permit liquid to readily penetrate through its thickness.

In one particular embodiment, the liner includes a nonwoven web formed in accordance with the present invention. Exemplary liner constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941, all of which are incorporated herein in their entirety by reference thereto for all purposes.

As illustrated in FIG. 1, the diaper 101 may also include a surge layer 107 that helps to decelerate and diffuse surges or gushes of liquid that may be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 may be located on an outwardly facing surface 118 of the bodyside liner 105. The surge layer 107 is typically constructed from highly liquid-permeable materials. Suitable materials may include porous woven materials, porous nonwoven materials, and apertured films. In one particular embodiment, the surge layer 107 includes a nonwoven web formed according to the present invention. Other examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

Besides the above-mentioned components, the diaper 101 may also contain various other components as is known in the art. For example, the diaper 101 may also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 103. The wrapsheet material on one side of the absorbent fibrous mass may be bonded to the wrapsheet located on the opposite side of the fibrous mass to effectively entrap the absorbent core 103.

The diaper 101 may also include a ventilation layer (not shown) that is positioned between the absorbent core 103 and the outer cover 117. When utilized, the ventilation layer may help insulate the outer cover 117 from the absorbent core 103, thereby reducing dampness in the outer cover 117. Examples of such ventilation layers may include a nonwoven web laminated to a breathable film, such as described in U.S. Pat. No. 6,663,611 to Blaney, et al., which is incorporated herein in its entirety by reference thereto for all purpose. Such nonwoven webs may be formed in accordance with the present invention.

The diaper 101 may also include a pair of ears (not shown) that extend from the side edges 132 of the diaper 101 into one of the waist regions. The ears may be integrally formed with a selected diaper component. For example, the ears may be integrally formed with the outer cover 117 or from the material employed to provide the top surface. In alternative configurations, the ears may be provided by members connected and assembled to the outer cover 117, the top surface, between the outer cover 117 and top surface, or in various other configurations. As representatively illustrated in FIG. 7, the diaper 101 may also include a pair of containment flaps 112 that are configured to provide a barrier and to contain the lateral flow of body exudates. The containment flaps 112 may be located along the laterally opposed side edges 132 of the bodyside liner 105 adjacent the side edges of the absorbent core 103. The containment flaps 112 may extend longitudinally along the entire length of the absorbent core 103, or may only extend partially along the length of the absorbent core 103. When the containment flaps 112 are shorter in length than the absorbent core 103, they may be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

The diaper 101 may include various elastic or stretchable materials, such as a pair of leg elastic members 106 affixed to the side edges 132 to further prevent leakage of body exudates and to support the absorbent core 103. In addition, a pair of waist elastic members 108 may be affixed to longitudinally opposed waist edges 115 of the diaper 101. The leg elastic members 106 and the waist elastic members 108 are generally adapted to closely fit about the legs and waist of the wearer in use to maintain a positive, contacting relationship with the wearer and to effectively reduce or eliminate the leakage of body exudates from the diaper 101. As used herein, the terms "elastic" and "stretchable" include any material that may be stretched and return to its original shape when relaxed. Suitable polymers for forming such materials include, but are not limited to, block copolymers of polystyrene, polyisoprene and polybutadiene; copolymers of ethylene, natural rubbers and urethanes, etc. Particularly suitable are styrene-butadiene block copolymers sold by Kraton Polymers of Houston, Tex. under the trade name Kraton®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels.

The diaper 101 may also include one or more fasteners 130. For example, two flexible fasteners 130 are illustrated in FIG. 7 on opposite side edges of waist regions to create a waist opening and a pair of leg openings about the wearer. The shape of the fasteners 130 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 130 includes a separate piece of hook material affixed to the inside surface of a flexible backing.

The various regions and/or components of the diaper 101 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 may be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, may also be assembled into the diaper 101 using any attachment mechanism.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes.

The present invention may be better understood with reference to the following examples.

Test Methods

Fecal Matter Collection

Real fecal matter was collected from 50 human babies. The collected fecal matter was combined and mixed together. Then, the resulting mixed fecal matter was separated into useful storage and testing sizes and frozen until needed.

Fecal Fluid Extract Preparation

Fluid was centrifuged out of a real fecal matter slurry having a mushy or pasty consistency at 7000 rpm for 30 minutes using a Sorvall RT 6000D centrifuge. About 10-20% of the weight of the initial fecal matter sample was extracted. For example, in this case, 40 g of fecal matter resulted in just shy of 5 g of Fecal Fluid Extract (FFE). This fluid was then centrifuged again in an Eppendorf Centrifuge 5514C at 10000 rpm for 10 minutes. The liquid was decanted off and frozen.

Fecal Fluid Extract Characterization

In order to understand the mechanism of adhesion, it is also important to understand the properties of the adherent. Therefore, the surface tension of the FFE was measured using a Kruss Tensiometer. The surface energy of VitroSkin and FFE were characterized in terms of dispersive and polar components using the Fowkes method and contact angles with known materials. The contact angle for each material with diiodomethane was also measured in order to have a complete polar/dispersive characterization for each material. Table 1 shows that most of the higher polar materials are the better performers. Some data may be suspect, like the spunbond control composite, due to the fact that it is a porous nonwoven, which makes contact angle measurements difficult and inaccurate due to various curvatures created from the porosity. The same can be said of the SB+Reten204LS, Cerex+Reten 204LS and the SB+Irgasurf. However more smooth surfaces like film give more accurate results.

TABLE I

Polar and Dispersive breakdown for select test materials

| | Solid | | | Contact Angle | | | | |
| --- | --- | --- | --- | --- | --- | --- | --- | --- |
| | | | | Diiodomethane | | FFE | | |
| | Polar | Dispersive | Total | Calculated | Measured | Calculated | Measured | Comments |
| PET | 3.06 | 42.05 | 45.11 | 29 | 29 | 48 | 48 | good agreement |
| Parafilm | 0.01 | 30.66 | 30.66 | 57 | 58 | 87 | 90 | good agreement |
| Vitro Skin | 0.08 | 41.09 | 41.17 | 38 | 38 | 75 | 75 | good agreement |
| Biodyne A | 0.19 | 42.66 | 42.86 | 34 | 34 | 71 | 71 | good agreement |
| Control composite | 11.08 | 40.61 | 51.69 | 24 | 52 | N/A | 136 | suspect FFE data |
| Biodyne B | 2.13 | 41.84 | 43.97 | 31 | 31 | 54 | 54 | good agreement |
| SB + Reten 204LS | 1.24 | 34.96 | 36.21 | 47 | 54 | 67 | 102 | fair agrmt, FFE data suspect |
| Whatman 41 | 6.98 | 40.19 | 47.17 | 29 | 29 | 28 | 28 | good agreement |
| Whatman DE81 | 6.80 | 40.26 | 47.06 | 29 | 29 | 29 | 29 | good agreement |
| Cerex + Reten 204LS | 5.12 | 57.57 | 62.69 | N/A | 0 | N/A | 102 | suspect data |
| SB + Irgasurf | 2.11 | 48.79 | 50.90 | 0 | 0 | 47 | 47 | good agreement |

It was found that fecal fluid extract from a slurry of mushy/pasty fecal matter has a surface tension of about 37.5 dynes/cm. The dispersive component of the fecal matter had a surface tension of about 12 dynes/cm. Also, the fecal matter had a polar component with a surface tension of about 25.5 dynes/cm.

The fecal matter had a particle size that was quite variable between individual samples. However, within each sample, the particle size was more consistent. All of the samples had particle sizes of between 0.1 microns to about 700 microns, as measured with a particle size analyzer sold under the name Microtrac X100 by Leeds & Northrup Co. of North Wales, Pa., although it is likely that some fecal matter particles are even larger than this. A majority of the fecal matter particles fell into two groups: (a) from about 1 micron to 3 microns and (b) from about 25 microns to about 500 microns.

Contact Angle Measurement Procedure

The sessile drop method, as well known in the art, was used to determine contact angle, as more specifically described below.

Goniometry equipment (Ramé-Hart Instrument Co., model 100-00-115) and high-magnification digital camera (Sony, DKC-5000 3CCD) were completely set up before beginning the contact angle measurements. A small, 100 uL pipette was suspended above the observation plate inside a larger syringe, which the pipette tip could fit through. This enabled the very tip of the pipette to be easily manipulated into position. The camera attachment was set to 2× zoom.

Frozen fecal fluid extract was thawed in a water bath for 3-4 hours at 37 degrees C. It was removed and allowed to acclimate to room temperature for 1 hour before use and left unopened underneath a hood.

Samples of each bodyside liner material were cut into 2"×2" squares. In lieu of 2"×2" squares, 2" diameter circles were also occasionally used. There was no apparent difference in measurements that were repeated with both.

A square sample of the material was placed on the observation plate, and the pipette was lowered so that the tip was just within the upper field of view of the camera. The camera was focused such that this tip was completely clear and in-focus. The droplet was placed directly below and was also in focus once released. The camera had less than half of the bottom portion of the field of view taken up by the material. No metal from the observation plate was visible, except in cases of exceptionally thin, clear material. The material needs to be flat in the area beneath the pipette. The lighting was adjusted for the best contrast between the material and the background.

Once the camera was appropriately focused, the pipette was removed from the syringe and brought to the hood where the room-temperature FFE was stored. The pipette was set to deliver 5 μL of fluid. The test tube containing the FFE was opened and the pipette piston was completely depressed to gather more than 5 μL of fluid. The FFE container was sealed, and the pipette was taken back to the goniometry equipment and placed in the syringe. The FFE was in-focus inside the tip of the pipette at the top of the camera's field of view.

The recording software, Pinnacle's Studio Version 9, was set to record 10 seconds of video. There was a delay between the pressing of the 'start recording' button and the actual beginning of the recording. The time is apparent in the software window. As soon as this counter started, the pipette was quickly depressed to the first resistance point, and 5 μL of fluid was deposited onto the material. Once the recording was complete, the frame immediately following the fluid's contact with the material and disconnection from the pipette was captured and saved as a .jpg file. The default was .bmp.

If the material rapidly absorbed the FFE (i.e., if it seemed instantaneously absorbed as observed by the eye), a series of frames was captured. The first was set for time t=1units, and the following frames were added at t=2, etc. for 5 frames. If the material was absorbing slowly enough, every other frame was captured, effectively being at time t=1, t=3, t=5, etc. for 5 frames. Each frame was 1/30 second after the previous one, and 1/15 second for every other frame.

Tweezers were used to pull the material around the observation plate until a clean, flat area was beneath the pipette. The procedure was repeated. This was done 3 times. After observations were complete, the material was removed from the plate with the tweezers. The plate was cleaned thoroughly with distilled water and 10% bleach solution after each completed test run.

Contact Angle Calculation

The contact angle is the angle starting from the inside of the bubble and progressing outside of the bubble to the sloped line. The .jpg captured frame was loaded into Image Pro Plus. A line was drawn horizontally across the material and just below the FFE bubble.

If the contact angle is clearly less than 90 degrees, a second line was drawn approximating the slope of the bubble at the intersection of the solid and the liquid material. It was easiest to draw this line directly on top of this intersection for simple reference. Several attempts were often required. Once the line matches the slope of the FFE bubble, the "angle between two features" measurement tool was used to measure the angle between the horizontal line and the sloped line. This angle was recorded. This was repeated for both the left and right sides of the bubble for each trial.

Figure 8:
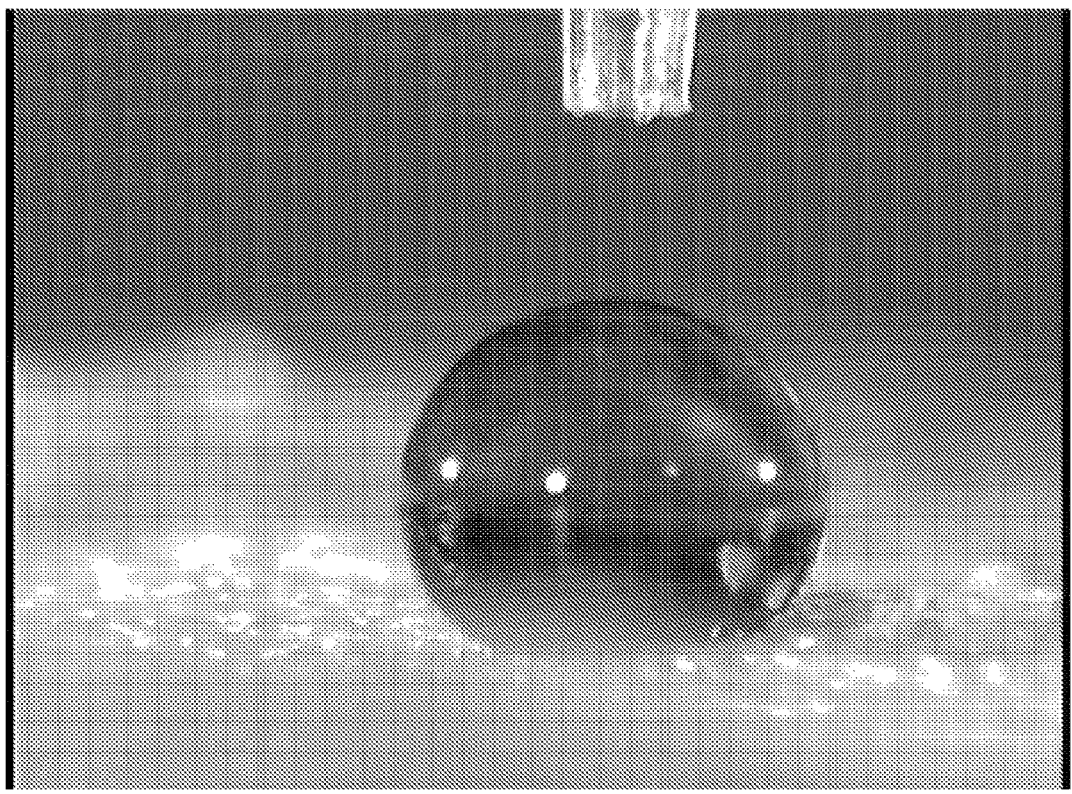
FIG. 8 is a picture of a fecal fluid extract droplet on a surface, as described in the Examples.
Figure 9:
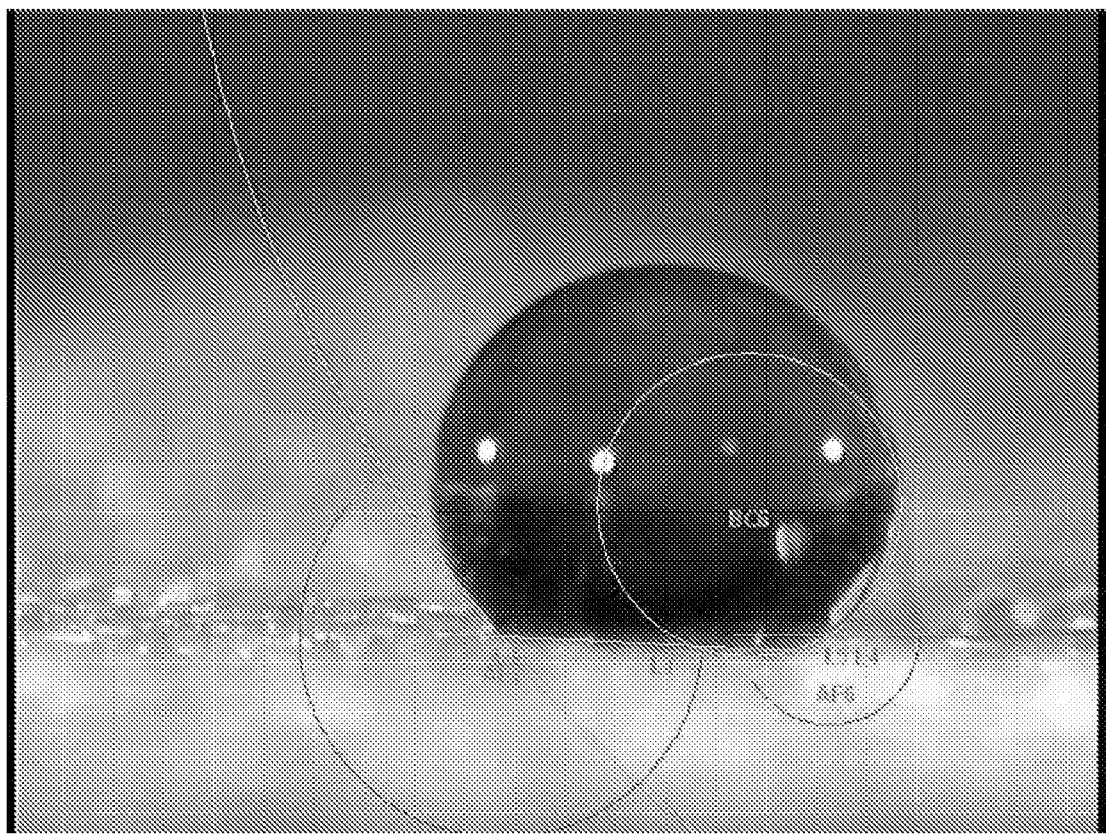
FIG. 9 is a picture of a fecal fluid extract droplet on a surface, along with the contact angle calculation lines added as described in the Examples.

This occasionally caused basic geometric calculations to be made when the program reported a different angle measurement. FIG. 8 is a picture of a fecal fluid extract droplet on a surface. A semi-circle is drawn to indicate which angle the program is measuring, as seen in FIG. 9. The right-side angle in FIG. 9 that the program is measuring is that which is directly opposite the contact angle. Geometrically, this has the same value, but it is important to notice what angle is being measured.

On the other hand, if the contact angle of a material was clearly greater than 90 degrees, a best-fit circle closely matching the curvature of the edge of each side of the FFE bubble near the point of contact with the liner material was created. The center x, y coordinates and the radius of this circle were displayed by Image Pro Plus and recorded. Knowing these values, the slope of any line tangent to the circle is:

$$D_y/d_x = -(X_{contact} - X_{center})/(Y_{contact} - Y_{center})$$

where $X_{contact}$ and $Y_{contact}$ are the coordinates of the point of contact between the drop and the liner material and $X_{center}$ and $Y_{center}$ are the circle's center-point coordinates. The program can give this position to the pixel.

Then, the X-values 10 units left and right of this point of contact were used to calculate the end points of a line tangent to the circle at that point of contact. The following equation was used:

$$Y_{endpoint} = Y_{contact} + \text{slope} * (X_{endpoint} - X_{contact})$$

where $X_{endpoint}$ and $Y_{endpoint}$ are the endpoint coordinates. This was done for both end points 10 units left and 10 units right of $X_{contact}$. A line was then drawn with these two calculated points as its endpoints and the angle was measured between this line and a horizontal line to use as the contact angle. FIG. 9 illustrates the results of this procedure. This was performed for all trials along both the left and right sides of the droplet. The contact angles were then averaged and that average was used in all future contact angle calculations.

If the droplet was absorbed into the material too quickly, it was necessary to measure the contact angle at several intervals during its absorption, typically every other frame. This corresponds to about every $\frac{1}{15}^{th}$ of a second. These points were graphed against time and extrapolated back to time 0, taken as the frame in which the droplet was first completely disconnected from the pipette, as demonstrated in FIG. 10.

Figure 10:
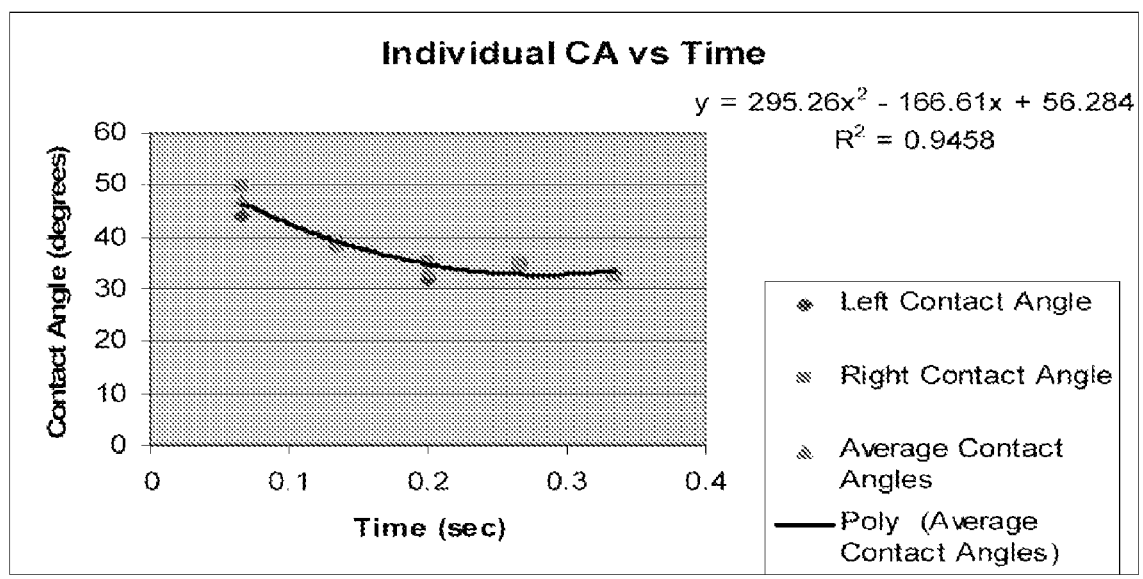
FIG. 10 is a graph of the contact angle plotted against time in order to determine the contact angle when the droplet first contacted the surface, as described in the Examples.

Rather than averaging the contact angles over the 5 frames, these contact angles were graphed against time, with the first frame at time t=1 units and the follow frames at time t=2, t=3, etc. An equation was generated for the curve fitting those data points and extrapolated back to time t=0. This y-intercept value was then used as the contact angle, such as shown in FIG. 10. These extrapolated values for each side of the bubble over 3 trials were averaged and used as the contact angle for all calculations.

Additional contact angles were measured on Parafilm, Teflon, and Polyester films, as well as VitroSkin for comparison to the experimental materials. Furthermore, diiodomethane was used to measure contact angle on all materials in order to determine the surface energy of each in terms of dispersive and polar characteristics. The surface energy of VitroSkin was previously undetermined and unlisted in literature.

Surface Energy Characterization

The surface energy of VitroSkin and FFE were characterized in terms of dispersive and polar components using the Fowkes method, which is described in detail in the following publication: Fowkes, F. M. "Attractive Forces At Interfaces", Industrial & Engineering Chemistry, Vol. 56, No. 12, Pages 40-52 (1964), and contact angle measurements with known materials. The contact angle each material has with diiodomethane was measured as well in order to have a complete polar/dispersive characterization of each.

Fecal Matter to Skin Adherence Test

In order to determine the ability of a composite bodyside liner sample to reduce the amount of fecal matter that adheres to the skin of the wearer after removal of the composite bodyside liner, a gravimetric test was performed. In this test, a mini, non-absorbent composite was put together for quick testing. This composite consisted of the test bodyside liner, which in control situations wound be a spunbond web of polypropylene fibers. Underneath this layer was a highly breathable stretch thermal laminate (HBSTL) outercover material, which is a film of polyethylen and calcium carbonate. All of these materials were ultrasonically bonded together in a 2"×2" square. All test composites, the Vitro-skin®, and the frozen fecal mater were allowed to thaw and/or acclimate for four hours inside an environmental chamber at 90° F. and 95% relative humidity (in an attempt to mimic and recreate the conditions inside a diaper when worn). Then, the particular composite bodyside liner sample to be tested was weighed prior to each sample testing. Also, a sample of Vitro-skin®, available from Innovative Measurement Solutions, Inc. (Milford, CT) was weighed prior to each sample testing.

A known amount of fecal matter (from 0.5 g to 1 g) was placed upon a Vitro-skin® sample laying flat on a surface. This was done using a Teflon template applied on top of the Vitro-skin® leaving a circular mass of fecal matter with a diameter of about ¾ inch and a thickness of about ⅛ inch. Then, the composite bodyside liner sample was placed on top of the soiled Vitro-skin®, and a 1 kg weight was placed on top of the composite bodyside liner sample. The composite bodyside liner was allowed to sit for 1 minute.

After the minute expired, the composite bodyside liner and Vitro-skin® were separately weighed, and the amount of fecal matter remaining on each was determined. Then, a percentage of the total fecal matter that remained on each was calculated.

Determining Material Caliper (Thickness):

The caliper of a material is a measure of thickness and is measured at 0.05 psi (3.5 g/cm$^2$) with a Starret® bulk tester, in units of millimeters. Samples are cut into 4 inch by 4 inch (10.2 cm by 10.2 cm) squares, five samples are tested, and the results averaged.

Materials

Each of the polar components used in the following Examples is briefly described in the following section:

Reten® 204LS (Hercules Inc., Wilmington, Del.): An aqueous solution of a cationic amine polymer-epichlorohydrin adduct having high charge and low molecular weight.

Kymene® 557LX (Hercules Inc., Wilmington, Del.): An aqueous solution of a cationic amine polymer-epichlorohydrin adduct popular as a binder in paper products. It was also the safest with the lowest residuals of all the Kymenes at the time; however, it has a lower net charge than Reten 204LS and a different chemical structure.

pAMPS: Polyacrylamidomethylpropane sulfonic acid is an amphoteric chemical.

PHMB: Polyhexamethylene biguanide is a positively charged polymer that is active against microorganisms.

Chitosan: Chitosan is a natural product derived from Chitin, a polysaccharide found in the exoskeleton of shellfish like shrimp or crabs and is cationic.

AEM 5700: 3-(trimehtyloxysilyl)propyloctadecyl ammonium chloride is an antimicrobial agent.

Snowtex® (Nissan Chemical America Corp., Houston, Tex.): A colloidal silica solution made by dispering negatively charged, amorphous silica paraspherical in shape. OH ions exist at the surface of the particles.

Crosultaine C-50: Cocamidopropyl hydroxysultaine is a mild, vegetable derived ampoteric surfactants based on the coco moieties.

Perform PC1279 (Hercules Inc., Wilmington, Del.): This chemical is available from Hercules as a high charge, low molecular weight cationic solution polymer.

Hercules 5153 (Hercules Inc., Wilmington, Del.): This chemical is an anionic solution polymer.

Hercules 5152 (Hercules Inc., Wilmington, Del.): This chemical is an anionic polyacrylamide solution polymer.

Also, each of the sheets used as samples of a fluid pervious liner layer or a surge layer in the following Examples is briefly described in the following section:

Spunbond Polypropylene:

Whatman® 41 (Whatman International, Ltd.) is an ashless quantitative filter having apertures of between about 20 μm and 25 μm in diameter, a thickness of about 215 μm, and a basis weight of about 84 g.m$^2$.

Whatman® DE 81 (Whatman International, Ltd.) is an ion exchange cellulose paper having a thickness of about 0.20 mm with a weakly basic anion exchanger having diethylaminoethyl functional groups. Its ion exchange capacity is reported as 1.7 μeq/cm$^2$ and flow rate is 95 mm per 30 mins.

Whatman® P81 (Whatman International, Ltd.) is an ion exchange cellulose phosphate paper having a thickness of about 0.23 mm. Its ion exchange capacity is reported as 18.0 μeq/cm$^2$ and flow rate is 125 mm per 30 mins.

Biodyne A (Pall Corp., NY) is an amphoteric nylon 6,6 membrane and pore sizes of 0.2, 0.45, and 1.2 μm.

Biodyne B (Pall Corp., NY) is a positively-charged nylon 6,6 membrane having pore surfaces populated by a high density of quaternary ammonium groups and pore sizes of 0.2, 0.45, and 1.2 μm.

Biodyne C (Pall Corp., NY) is a negatively-charged nylon 6,6 having carboxyl groups on the pore surfaces and pore sizes of 0.2, 0.45, and 1.2 μm.

Bemcot (Asahi Kasei Fibers Corp.) is a cellulose spunbond material having an average pore size that is a little greater then 100 microns, but some pores are even greater then 500 microns.

EXAMPLE 1

A few different chemicals, in varying amounts, were used for treating a sample of a polypropylene spunbond diaper liner. Each of the samples was then tested according to the Fecal Matter to Skin Adherence Test, as described above. Table 2 shows each sample, along with the amount of fecal matter used in each sample test, along with the calculated results:

TABLE 2

| Material | V-Skin Before (g) | Sample Before (g) | V-Skin with FFE (g) | Fecal Matter (g) | V-Skin after (g) | Sample after (g) | Fecal Matter Left on V-Skin (g) | Fecal Matter Left on Sample (g) | % Fecal Matter Left on Skin | % Fecal Matter Left on Sample |
|---|---|---|---|---|---|---|---|---|---|---|
| Control SB | 1.6299 | 0.955 | 2.3152 | 0.685 | 2.2002 | 0.9577 | 0.5703 | 0.0027 | 83 | 0 |
| Control SB | 1.7142 | 0.4987 | 2.275 | 0.561 | 2.1496 | 0.6055 | 0.4354 | 0.1068 | 78 | 19 |
| Control SB | 1.8456 | 0.4612 | 2.4904 | 0.645 | 2.366 | 0.5608 | 0.5204 | 0.0996 | 81 | 15 |
| Control SB | 1.8972 | 0.4728 | 2.5151 | 0.618 | 2.3516 | 0.5909 | 0.4544 | 0.1181 | 74 | 19 |
| Control SB | 1.8568 | 0.4867 | 2.3622 | 0.505 | 2.2412 | 0.5871 | 0.3844 | 0.1004 | 76 | 20 |
| Stdev | 0.1 | 0.2 | 0.1 | 0.1 | 0.1 | 0.2 | 0.1 | 0.0 | 3.8 | 8.2 |
| % CV | 6.3 | 37.0 | 4.5 | 11.7 | 4.2 | 25.3 | 15.4 | 54.8 | 4.9 | 55.6 |
| Average | 1.8 | 0.6 | 2.4 | 0.6 | 2.3 | 0.7 | 0.5 | 0.1 | 78.2 | 14.8 |
| SB + Kymene ® 557 LX 10% | 1.7287 | 0.4796 | 2.5026 | 0.774 | 2.2622 | 0.6843 | 0.5335 | 0.2047 | 69 | 26 |
| SB + Kymene ® 557 LX 10% | 2.9824 | 0.4647 | 3.5062 | 0.524 | 3.296 | 0.6387 | 0.3136 | 0.174 | 60 | 33 |
| SB + Kymene 557 LX 10% | 2.3087 | 0.5198 | 3.0137 | 0.705 | 2.8852 | 0.6194 | 0.5765 | 0.0996 | 82 | 14 |
| SB + Kymene 557 LX 10% | 1.9416 | 0.4706 | 2.5034 | 0.562 | 2.4192 | 0.5519 | 0.4776 | 0.0813 | 85 | 14 |
| SB + Kymene 557 LX 10% | 1.9258 | 0.525 | 2.6043 | 0.679 | 2.5321 | 0.6227 | 0.6063 | 0.0977 | 89 | 14 |
| Stdev | 0.5 | 0.0 | 0.4 | 0.1 | 0.4 | 0.0 | 0.1 | 0.1 | 12.2 | 8.8 |
| % CV | 22.8 | 5.8 | 15.4 | 16.0 | 15.5 | 7.6 | 23.1 | 41.4 | 15.9 | 43.0 |
| Average | 2.2 | 0.5 | 2.8 | 0.6 | 2.7 | 0.6 | 0.5 | 0.1 | 77.0 | 20.5 |
| SB + 1.4% Reten ® 204LS | 2.7228 | 0.5205 | 3.554 | 0.831 | 3.1965 | 0.8211 | 0.4737 | 0.3006 | 57 | 36 |
| SB + 1.4% Reten ® 204LS | 2.7069 | 0.5017 | 3.6313 | 0.924 | 3.0913 | 0.9814 | 0.3844 | 0.4797 | 42 | 52 |
| SB + 1.4% Reten ® 204LS | 2.8262 | 0.4845 | 3.5462 | 0.72 | 3.2026 | 0.7614 | 0.3764 | 0.2769 | 52 | 38 |
| SB + 1.4% Reten ® 204LS | 2.683 | 0.4915 | 3.2431 | 0.56 | 3.0382 | 0.6596 | 0.3552 | 0.1681 | 63 | 30 |
| SB + 1.4% Reten ® 204LS | 2.5604 | 0.524 | 3.0843 | 0.524 | 2.854 | 0.7155 | 0.2936 | 0.1915 | 56 | 37 |
| Stdev | 0.1 | 0.0 | 0.2 | 0.2 | 0.1 | 0.1 | 0.1 | 0.1 | 8.0 | 8.1 |
| % CV | 3.5 | 3.5 | 6.9 | 24.1 | 4.6 | 15.7 | 17.2 | 43.4 | 14.9 | 20.9 |
| Average | 2.7 | 0.5 | 3.4 | 0.7 | 3.1 | 0.8 | 0.4 | 0.3 | 54.1 | 38.6 |
| SB + 5% Reten ® 204LS | 2.1215 | 0.495 | 2.797 | 0.676 | 2.5817 | 0.6943 | 0.4602 | 0.1993 | 68 | 30 |
| SB + 5% Reten ® 204LS | 1.9045 | 0.506 | 2.512 | 0.608 | 2.2912 | 0.715 | 0.3867 | 0.209 | 64 | 34 |
| SB + 5% Reten ® 204LS | 1.8712 | 0.497 | 2.4333 | 0.562 | 2.2845 | 0.6311 | 0.4133 | 0.1341 | 74 | 24 |
| SB + 5% Reten ® 204LS | 1.7467 | 0.4406 | 2.3496 | 0.603 | 2.1779 | 0.6022 | 0.4312 | 0.1616 | 72 | 27 |

TABLE 2-continued

| Material | V-Skin Before (g) | Sample Before (g) | V-Skin with FFE (g) | Fecal Matter (g) | V-Skin after (g) | Sample after (g) | Fecal Matter Left on V-Skin (g) | Fecal Matter Left on Sample (g) | % Fecal Matter Left on Skin | % Fecal Matter Left on Sample |
|---|---|---|---|---|---|---|---|---|---|---|
| SB + 5% Reten® 204LS | 1.986 | 0.4734 | 2.6447 | 0.659 | 2.4726 | 0.633 | 0.4866 | 0.1596 | 74 | 24 |
| Stdev | 0.1 | 0.0 | 0.2 | 0.0 | 0.2 | 0.0 | 0.0 | 0.0 | 4.3 | 4.4 |
| % CV | 7.2 | 5.4 | 6.9 | 7.4 | 6.9 | 7.2 | 9.0 | 17.9 | 6.1 | 15.7 |
| Average | 1.9 | 0.5 | 2.5 | 0.6 | 2.4 | 0.7 | 0.4 | 0.2 | 70.1 | 27.8 |
| SB + 20% Reten® 204LS | 2.4164 | 0.4647 | 3.4065 | 0.99 | 2.9486 | 0.8924 | 0.5322 | 0.4277 | 54 | 43 |
| SB + 20% Reten® 204LS | 2.2391 | 0.485 | 3.0559 | 0.817 | 2.6221 | 0.8999 | 0.383 | 0.4149 | 47 | 51 |
| SB + 20% Reten® 204LS | 1.875 | 0.4622 | 2.6357 | 0.761 | 2.2657 | 0.8165 | 0.3907 | 0.3543 | 51 | 47 |
| SB + 20% Reten® 204LS | 1.851 | 0.4854 | 2.8814 | 1.03 | 2.4139 | 0.936 | 0.5629 | 0.4506 | 55 | 44 |
| SB + 20% Reten® 204LS | 2.66 | 0.5121 | 3.2615 | 0.602 | 2.8266 | 0.9169 | 0.1666 | 0.4048 | 28 | 67 |
| Stdev | 0.3 | 0.0 | 0.3 | 0.2 | 0.3 | 0.0 | 0.2 | 0.0 | 11.1 | 10.0 |
| % CV | 15.8 | 4.2 | 10.0 | 20.8 | 10.8 | 5.1 | 38.6 | 8.7 | 23.7 | 19.8 |
| Average | 2.2 | 0.5 | 3.0 | 0.8 | 2.6 | 0.9 | 0.4 | 0.4 | 46.9 | 50.3 |
| SB + 15% Reten® 204LS | 2.2412 | 0.5042 | 2.7714 | 0.53 | 2.52 | 0.7356 | 0.2788 | 0.2314 | 53 | 44 |
| SB + 15% Reten® 204LS | 2.2933 | 0.499 | 3.0639 | 0.771 | 2.684 | 0.84 | 0.3907 | 0.341 | 51 | 44 |
| SB + 15% Reten® 204LS | 2.1849 | 0.518 | 3.1584 | 0.974 | 2.52 | 1.1352 | 0.3351 | 0.6172 | 34 | 63 |
| SB + 15% Reten® 204LS | 2.334 | 0.534 | 2.9453 | 0.611 | 2.5625 | 0.8719 | 0.2285 | 0.3379 | 37 | 55 |
| SB + 15% Reten® 204LS | 1.7659 | 0.445 | 2.5295 | 0.764 | 2.3481 | 0.61 | 0.5822 | 0.165 | 76 | 22 |
| Stdev | 0.2 | 0.0 | 0.2 | 0.2 | 0.1 | 0.2 | 0.1 | 0.2 | 16.6 | 15.7 |
| % CV | 10.6 | 6.7 | 8.6 | 23.3 | 4.8 | 23.2 | 37.7 | 51.0 | 33.0 | 34.5 |
| Average | 2.2 | 0.5 | 2.9 | 0.7 | 2.5 | 0.8 | 0.4 | 0.3 | 50.3 | 45.6 |
| SB + 10% Reten® 204LS | 3.3341 | 0.4889 | 3.8322 | 0.498 | 3.5302 | 0.7501 | 0.1961 | 0.2612 | 39 | 52 |
| SB + 10% Reten® 204LS | 2.3855 | 0.5033 | 3.2214 | 0.836 | 2.6556 | 1.0291 | 0.2701 | 0.5258 | 32 | 63 |
| SB + 10% Reten® 204LS | 2.7447 | 0.4991 | 3.7243 | 0.98 | 3.3273 | 0.8614 | 0.5826 | 0.3623 | 59 | 37 |
| SB + 10% Reten® 204LS | 2.4046 | 0.4606 | 2.9926 | 0.588 | 2.7546 | 0.6877 | 0.35 | 0.2271 | 60 | 39 |
| SB + 10% Reten® 204LS | 2.4102 | 0.5352 | 3.1044 | 0.694 | 2.7354 | 0.8479 | 0.3252 | 0.3127 | 47 | 45 |
| Stdev | 0.4 | 0.0 | 0.4 | 0.2 | 0.4 | 0.1 | 0.1 | 0.1 | 12.1 | 10.7 |
| % CV | 15.3 | 5.4 | 11.2 | 26.8 | 13.3 | 15.5 | 42.2 | 34.6 | 25.5 | 22.6 |
| Average | 2.7 | 0.5 | 3.4 | 0.7 | 3.0 | 0.8 | 0.3 | 0.3 | 47.5 | 47.2 |

As shown in these results, polypropylene spunbond layers having Reten® applied to the layer, instead of Kymene® performed better, due to the fact that Reten® is more highly charged than Kymene®. Also, the at level of add-on of the Reten® is shown to influence the amount of FFE retained by the layer. For instance, the samples where the Reten® is added at levels of between 10% by weight and 20% by weight performed significantly better than the samples having Reten® applied at only 5% by weight.

EXAMPLE 2

In this example, several different liquid pervious liner materials were tested. Each material was prepared and tested according to the Fecal Matter to Skin Adherence Test, except that no fecal adhering treatment composition was applied to any sample due to the chemical treatments provided by the manufacturer of each material. The results are shown in Table 3:

| Material | V-Skin Before (g) | Mat. Before (g) | V-Skin with FFE (g) | Fecal Matter (g) | V-Skin after (g) | Mat. after (g) | FM Left on V-Skin (g) | FM Left on Mat. (g) | % FM Left on Skin | % FM Left on Mat. |
|---|---|---|---|---|---|---|---|---|---|---|
| Biodyne A | 1.5853 | 0.6185 | 2.228 | 0.642 | 2.16 | 0.663 | 0.579 | 0.045 | 90 | 7 |
| Biodyne A | 2.4451 | 0.6066 | 3.203 | 0.758 | 3.12 | 0.659 | 0.684 | 0.052 | 90 | 7 |
| Biodyne A | 1.6337 | 0.5907 | 2.306 | 0.673 | 2.21 | 0.662 | 0.586 | 0.071 | 87 | 11 |
| Biodyne A | 1.5632 | 0.6467 | 2.239 | 0.675 | 2.20 | 0.691 | 0.645 | 0.044 | 95 | 7 |
| Stdev | 0.4 | 0.0 | 0.5 | 0.0 | 0.5 | 0.0 | 0.1 | 0.0 | 3.5 | 1.9 |
| % CV | 23.6 | 3.8 | 19.0 | 7.2 | 19.2 | 2.2 | 8.0 | 23.6 | 3.8 | 24.5 |
| Average | 1.8 | 0.6 | 2.5 | 0.7 | 2.4 | 0.7 | 0.6 | 0.1 | 90.7 | 7.8 |
| Biodyne B | 1.452 | 0.6292 | 2.100 | 0.648 | 1.88 | 0.82 | 0.431 | 0.191 | 66 | 29 |
| Biodyne B | 1.8472 | 0.6668 | 2.368 | 0.521 | 2.24 | 0.749 | 0.402 | 0.082 | 77 | 16 |
| Biodyne B | 1.689 | 0.6463 | 2.396 | 0.707 | 2.19 | 0.820 | 0.502 | 0.174 | 71 | 25 |
| Biodyne B | 1.7296 | 0.6564 | 2.557 | 0.827 | 2.30 | 0.882 | 0.578 | 0.226 | 70 | 27 |
| Stdev | 0.2 | 0.0 | 0.2 | 0.1 | 0.2 | 0.1 | 0.1 | 0.1 | 4.4 | 6.0 |
| % CV | 9.9 | 2.5 | 8.0 | 18.8 | 8.8 | 6.7 | 16.5 | 36.4 | 6.2 | 24.6 |
| Average | 1.7 | 0.6 | 2.4 | 0.7 | 2.2 | 0.8 | 0.5 | 0.2 | 71.1 | 24.3 |
| Biodyne C | 1.8871 | 0.6153 | 2.397 | 0.51 | 2.29 | 0.701 | 0.401 | 0.085 | 79 | 17 |
| Biodyne C | 1.81 | 0.5896 | 2.391 | 0.581 | 2.22 | 0.738 | 0.412 | 0.148 | 71 | 26 |
| Biodyne C | 2.0447 | 0.5851 | 2.612 | 0.568 | 2.43 | 0.734 | 0.387 | 0.149 | 68 | 26 |
| Biodyne C | 1.8213 | 0.5872 | 2.467 | 0.646 | 2.24 | 0.781 | 0.420 | 0.194 | 65 | 30 |
| Biodyne C | 1.9751 | 0.5635 | 2.625 | 0.650 | 2.40 | 0.763 | 0.423 | 0.200 | 65 | 31 |
| Stdev | 0.1 | 0.0 | 0.1 | 0.1 | 0.1 | 0.0 | 0.0 | 0.0 | 5.6 | 5.6 |
| % CV | 5.3 | 3.1 | 4.6 | 9.9 | 4.1 | 4.1 | 3.6 | 29.6 | 8.1 | 21.6 |
| Average | 1.9 | 0.6 | 2.5 | 0.6 | 2.3 | 0.7 | 0.4 | 0.2 | 69.6 | 25.9 |
| P81 | 1.9243 | 0.7181 | 2.4657 | 0.541 | 2.31 | 0.862 | 0.390 | 0.144 | 72 | 27 |
| P81 | 1.9883 | 0.7404 | 2.9204 | 0.932 | 2.36 | 1.236 | 0.377 | 0.496 | 40 | 53 |
| P81 | 1.9441 | 0.7957 | 2.5405 | 0.596 | 2.25 | 1.038 | 0.307 | 0.2435 | 51 | 41 |
| P81 | 1.7034 | 0.7158 | 2.645 | 0.942 | 2.22 | 1.124 | 0.515 | 0.408 | 55 | 43 |
| Stdev | 0.1 | 0.0 | 0.2 | 0.2 | 0.1 | 0.2 | 0.1 | 0.2 | 7.5 | 6.6 |
| % CV | 6.7 | 5.0 | 7.5 | 28.4 | 2.9 | 14.8 | 21.8 | 49.2 | 15.4 | 14.5 |
| Average | 1.9 | 0.7 | 2.6 | 0.8 | 2.3 | 1.1 | 0.4 | 0.3 | 48.9 | 45.7 |
| DE81 | 1.8753 | 0.7502 | 2.507 | 0.632 | 2.12 | 1.215 | 0.247 | 0.465 | 39 | 73 |
| DE81 | 2.1459 | 0.7297 | 2.838 | 0.692 | 2.45 | 1.083 | 0.303 | 0.353 | 44 | 51 |
| DE81 | 2.347 | 0.7039 | 2.979 | 0.632 | 2.44 | 1.186 | 0.093 | 0.482 | 15 | 76 |
| DE81 | 2.2555 | 0.7453 | 2.906 | 0.650 | 2.28 | 1.285 | 0.026 | 0.539 | 4 | 83 |
| DE81 | 2.2107 | 0.7194 | 2.919 | 0.708 | 2.41 | 1.173 | 0.203 | 0.454 | 29 | 64 |
| Stdev | 0.2 | 0.0 | 0.2 | 0.0 | 0.1 | 0.1 | 0.1 | 0.1 | 16.6 | 12.4 |
| % CV | 8.2 | 2.6 | 6.6 | 5.3 | 6.0 | 6.1 | 65.1 | 14.7 | 63.9 | 17.8 |
| Average | 2.2 | 0.7 | 2.8 | 0.7 | 2.3 | 1.2 | 0.2 | 0.5 | 26.0 | 69.6 |
| Whatman 41 | 2.064 | 0.7126 | 2.620 | 0.556 | 2.29 | 1.016 | 0.231 | 0.303 | 42 | 55 |
| Whatman 41 | 1.9593 | 0.7491 | 2.731 | 0.771 | 2.25 | 1.205 | 0.293 | 0.456 | 38 | 59 |
| Whatman 41 | 2.1838 | 0.754 | 2.892 | 0.708 | 2.47 | 1.158 | 0.286 | 0.404 | 40 | 57 |
| Whatman 41 | 2.0522 | 1.0163 | 3.096 | 1.043 | 2.47 | 1.621 | 0.414 | 0.604 | 40 | 58 |
| Whatman 41 | 2.6668 | 0.7412 | 3.541 | 0.874 | 2.76 | 1.511 | 0.095 | 0.770 | 11 | 88 |
| Stdev | 0.3 | 0.1 | 0.4 | 0.2 | 0.2 | 0.3 | 0.1 | 0.2 | 13.1 | 13.9 |
| % CV | 12.8 | 15.7 | 12.2 | 23.1 | 8.2 | 19.5 | 43.8 | 36.0 | 38.3 | 22.0 |
| Average | 2.2 | 0.8 | 3.0 | 0.8 | 2.4 | 1.3 | 0.3 | 0.5 | 34.1 | 63.3 |
| Bemcot | 0.5378 | 0.6208 | 1.38 | 0.842 | 0.72 | 1.271 | 0.178 | 0.650 | 21 | 77 |
| Bemcot | 0.3791 | 0.6406 | 1.137 | 0.758 | 0.62 | 1.163 | 0.243 | 0.522 | 32 | 69 |
| Bemcot | 0.54 | 0.6269 | 1.279 | 0.739 | 0.75 | 1.145 | 0.208 | 0.518 | 28 | 70 |
| Bemcot | 0.6046 | 0.6343 | 1.296 | 0.691 | 0.75 | 1.173 | 0.144 | 0.538 | 21 | 78 |
| Bemcot | 0.3871 | 0.6288 | 0.933 | 0.546 | 0.56 | 1.002 | 0.178 | 0.373 | 33 | 68 |
| Stdev | 0.1 | 0.0 | 0.2 | 0.1 | 0.1 | 0.1 | 0.0 | 0.1 | 5.7 | 4.7 |
| % CV | 20.6 | 1.2 | 14.6 | 15.3 | 12.2 | 8.4 | 19.5 | 19.0 | 21.1 | 6.4 |
| Average | 0.5 | 0.6 | 1.2 | 0.7 | 0.7 | 1.2 | 0.2 | 0.5 | 27.0 | 72.5 |

As can be seen from the data, the positive, Biodyne B, and negative, Biodyne C, perform better then the neutral Biodyne A membrane due to an increase in polarity. All three filter papers from Whatman showed good results, which is believed to be largely due to their low contact angle, and high polarity. They also have a pore size around 20 microns as opposed to the much smaller pore size in the Biodyne membranes. Specifically, Whatman DE81 performed the best, which is believed to be due to its higher polarity from the diethyl-amine-ethyl which was added to the base filter paper. Also, the cellulose based material, Bemcot, which has bigger pore sizes then Whatman, allowed for better capture of big particles in the BM, while still maintaining a polar component due to the cellulose.

Biodyne B, Whatman 41, and Whatman DE 81 all show high polar numbers in Table 3. They are also all decent to great performers. As mentioned earlier the small pore size and smooth topography are the features that hinder Biodyne B from being a great performer. This shows good correlation with the idea that increasing the polarity of a material will help to increase the amount of fecal matter that adheres to it.

EXAMPLE 3

In this example, several different bodyside liners were tested, with and without a surge layer present. Each material was prepared and tested according to the Fecal Matter to Skin Adherence Test. The results are shown in Table 4:

TABLE 4

| Material | Skin Before (g) | Mat. Before (g) | Skin with BM (g) | BM (g) | Skin after (g) | Mat. after (g) | BM Left on Skin (g) | BM Left on Mat. (g) | % BM Left on Skin | % BM Left on Mat. |
|---|---|---|---|---|---|---|---|---|---|---|
| Composite control | 0.4425 | 0.4562 | 1.234 | 0.7915 | 0.878 | 0.8066 | 0.4359 | 0.3504 | 55 | 44 |
| Composite control | 0.3557 | 0.4857 | 1.4112 | 1.0555 | 0.938 | 0.9536 | 0.5826 | 0.4679 | 55 | 44 |
| Composite control | 0.3658 | 0.4769 | 1.2197 | 0.8539 | 0.562 | 1.1302 | 0.1957 | 0.6533 | 23 | 77 |
| Composite control | 0.3604 | 0.4893 | 1.2578 | 0.8974 | 0.78 | 1.0084 | 0.4196 | 0.5191 | 47 | 58 |
| Composite control | 0.3762 | 0.4793 | 1.204 | 0.8278 | 0.698 | 0.9864 | 0.3219 | 0.5071 | 39 | 61 |
| Stdev | 0.0 | 0.0 | 0.1 | 0.1 | 0.1 | 0.1 | 0.1 | 0.1 | 13.5 | 13.4 |
| % CV | 9.4 | 2.7 | 6.6 | 11.6 | 19.3 | 11.9 | 36.7 | 21.8 | 30.8 | 23.6 |
| Average | 0.4 | 0.5 | 1.3 | 0.9 | 0.8 | 1.0 | 0.4 | 0.5 | 43.8 | 56.8 |
| Coapertured SB on 3.0 osy surge | 0.3776 | 0.4497 | 1.3858 | 1.0082 | 1.043 | 0.7865 | 0.6649 | 0.3368 | 66 | 33 |
| Coapertured SB on 3.0 osy surge | 0.3609 | 0.4431 | 1.0505 | 0.6896 | 0.773 | 0.7159 | 0.4121 | 0.2728 | 60 | 40 |
| Coapertured SB on 3.0 osy surge | 0.3546 | 0.4424 | 1.1177 | 0.7631 | 0.606 | 0.9338 | 0.2513 | 0.4914 | 33 | 64 |
| Coapertured SB on 3.0 osy surge | 0.3641 | 0.3989 | 1.0604 | 0.6963 | 0.773 | 0.6815 | 0.4089 | 0.2826 | 59 | 41 |
| Coapertured SB on 3.0 osy surge | 0.3593 | 0.4259 | 1.4213 | 1.062 | 0.724 | 1.1197 | 0.3651 | 0.6938 | 34 | 65 |
| Stdev | 0.0 | 0.0 | 0.2 | 0.2 | 0.2 | 0.2 | 0.2 | 0.2 | 15.5 | 15.1 |
| % CV | 2.4 | 4.7 | 15.0 | 21.1 | 20.4 | 21.3 | 36.0 | 43.0 | 30.8 | 30.9 |
| Average | 0.4 | 0.4 | 1.2 | 0.8 | 0.8 | 0.8 | 0.4 | 0.4 | 50.3 | 48.7 |
| Coapertured SB + 10% Reten204LS on 3.0 osy surge | 0.3718 | 0.5721 | 1.0453 | 0.6735 | 0.814 | 0.771 | 0.4419 | 0.1989 | 66 | 30 |
| Coapertured SB + 10% Reten204LS on 3.0 osy surge | 0.3606 | 0.458 | 0.8999 | 0.5393 | 0.653 | 0.7096 | 0.2922 | 0.2516 | 54 | 47 |
| Coapertured SB + 10% Reten204LS on 3.0 osy surge | 0.4176 | 0.4927 | 1.454 | 1.0364 | 0.765 | 1.1836 | 0.347 | 0.6909 | 33 | 67 |
| Coapertured SB + 10% Reten204LS on 3.0 osy surge | 0.382 | 0.4891 | 1.3421 | 0.9601 | 0.671 | 1.1573 | 0.2891 | 0.6682 | 30 | 70 |
| Coapertured SB + 10% Reten204LS on 3.0 osy surge | 0.3661 | 0.4515 | 1.1127 | 0.7466 | 0.814 | 0.7583 | 0.4474 | 0.3068 | 60 | 41 |
| Stdev | 0.0 | 0.0 | 0.2 | 0.2 | 0.1 | 0.2 | 0.1 | 0.2 | 16.0 | 17.1 |
| % CV | 6.0 | 9.7 | 19.2 | 25.9 | 10.4 | 25.5 | 21.3 | 56.0 | 32.8 | 33.7 |
| Average | 0.4 | 0.5 | 1.2 | 0.8 | 0.7 | 0.9 | 0.4 | 0.4 | 48.7 | 50.7 |
| Coapertured SB on 3.0 osy surge + 10% Reten204LS | 0.3775 | 0.4717 | 1.3523 | 0.9748 | 0.689 | 1.1242 | 0.3115 | 0.6525 | 32 | 67 |

TABLE 4-continued

| Material | Skin Before (g) | Mat. Before (g) | Skin with BM (g) | BM (g) | Skin after (g) | Mat. after (g) | BM Left on Skin (g) | BM Left on Mat. (g) | % BM Left on Skin | % BM Left on Mat. |
|---|---|---|---|---|---|---|---|---|---|---|
| Coapertured SB on 3.0 osy surge + 10% Reten204LS | 0.3661 | 0.4465 | 1.1383 | 0.7722 | 0.617 | 0.961 | 0.2509 | 0.5145 | 32 | 67 |
| Coapertured SB on 3.0 osy surge + 10% Reten204LS | 0.3771 | 1.1773 | 1.2621 | 0.885 | 0.643 | 1.954 | 0.2658 | 0.7767 | 30 | 88 |
| Coapertured SB on 3.0 osy surge + 10% Reten204LS | 0.3648 | 0.4637 | 1.1697 | 0.8049 | 0.511 | 1.1211 | 0.1462 | 0.6574 | 18 | 82 |
| Coapertured SB on 3.0 osy surge + 10% Reten204LS | 0.4252 | 0.4484 | 1.2643 | 0.8391 | 0.672 | 1.034 | 0.2464 | 0.5856 | 29 | 70 |
| Stdev | 0.0 | 0.3 | 0.1 | 0.1 | 0.1 | 0.4 | 0.1 | 0.1 | 5.9 | 9.6 |
| % CV | 6.5 | 53.5 | 6.9 | 9.2 | 11.2 | 32.7 | 24.8 | 15.3 | 20.7 | 12.9 |
| Average | 0.4 | 0.6 | 1.2 | 0.9 | 0.6 | 1.2 | 0.2 | 0.6 | 28.4 | 74.6 |

In this example, it is obvious that the coapertured Spunbond surge+10% Reten 204LS performs the best. In this case the coapertured spunbond does not perform significantly better unless the Reten 204LS is placed on the surge. The believed reason behind this is that when water from the high humidity environment condensates on the liner it mitigates the effects of Reten 204LS. However when Reten 204LS is covered by an apertured layer water does not completely cover and mitigate the Reten 204LS and therefore allows it to react with fecal matter.

EXAMPLE 4

In this example, several different liquid pervious liner materials were tested. Each material was prepared and tested according to the Fecal Matter to Skin Adherence Test. The results are shown in Table 5:

| Material | Skin Before (g) | Mat. Before (g) | Skin with BM (g) | BM (g) | Skin after (g) | Mat. after (g) | BM Left on Skin (g) | BM Left on Mat. (g) | % BM Left on Skin | % BM Left on Mat. |
|---|---|---|---|---|---|---|---|---|---|---|
| Comp. control | 0.5124 | 0.4653 | 1.3179 | 0.8055 | 1.149 | 0.6203 | 0.6366 | 0.155 | 79 | 19 |
| Comp. control | 0.4975 | 0.4912 | 1.2503 | 0.7528 | 1.0684 | 0.6682 | 0.5709 | 0.177 | 76 | 24 |
| Comp. control | 0.4912 | 0.499 | 1.3955 | 0.9043 | 0.8752 | 1.0108 | 0.384 | 0.5118 | 42 | 57 |
| Comp. control | 0.509 | 0.4752 | 1.4717 | 0.9627 | 1.2605 | 0.6804 | 0.7515 | 0.2052 | 78 | 21 |
| Comp. control | 0.54 | 0.481 | 1.0459 | 0.5059 | 0.9497 | 0.5678 | 0.4097 | 0.0868 | 81 | 17 |
| Stdev | 0.0 | 0.0 | 0.2 | 0.2 | 0.2 | 0.2 | 0.2 | 0.2 | 16.2 | 16.4 |
| % CV | 3.7 | 2.7 | 12.6 | 22.5 | 14.5 | 24.6 | 28.1 | 72.6 | 22.7 | 59.5 |
| Average | 0.5 | 0.5 | 1.3 | 0.8 | 1.1 | 0.7 | 0.6 | 0.2 | 71.3 | 27.6 |
| SB + 10% Reten 204LS | 0.5363 | 0.4832 | 1.417 | 0.8807 | 1.1004 | 0.7915 | 0.5641 | 0.3083 | 64 | 35 |
| SB + 10% Reten 204LS | 0.5009 | 0.5434 | 1.2122 | 0.7113 | 1.0152 | 0.6886 | 0.5143 | 0.1452 | 72 | 20 |
| SB + 10% Reten 204LS | 0.502 | 0.5124 | 1.1736 | 0.6716 | 0.9015 | 0.7775 | 0.3995 | 0.2651 | 59 | 39 |
| SB + 10% Reten 204LS | 0.5177 | 0.5024 | 1.2479 | 0.7302 | 0.9206 | 0.8209 | 0.4029 | 0.3185 | 55 | 44 |
| SB + 10% Reten 204LS | 0.5666 | 0.5205 | 1.2048 | 0.6382 | 0.8529 | 0.8611 | 0.2863 | 0.3406 | 45 | 53 |
| Stdev | 0.0 | 0.0 | 0.1 | 0.1 | 0.1 | 0.1 | 0.1 | 0.1 | 10.2 | 12.1 |
| % CV | 5.2 | 4.3 | 7.7 | 12.8 | 10.3 | 8.1 | 25.1 | 28.3 | 17.3 | 31.6 |
| Average | 0.5 | 0.5 | 1.3 | 0.7 | 1.0 | 0.8 | 0.4 | 0.3 | 59.2 | 38.4 |
| Creped SB | 0.5009 | 0.5466 | 1.1852 | 0.6843 | 1.0381 | 0.8082 | 0.5372 | 0.2616 | 79 | 38 |

| Material | Skin Before (g) | Mat. Before (g) | Skin with BM (g) | BM (g) | Skin after (g) | Mat. after (g) | BM Left on Skin (g) | BM Left on Mat. (g) | % BM Left on Skin | % BM Left on Mat. |
|---|---|---|---|---|---|---|---|---|---|---|
| Creped SB | 0.5164 | 0.5421 | 1.3311 | 0.8147 | 0.9986 | 0.8713 | 0.4822 | 0.3292 | 59 | 40 |
| Creped SB | 0.5385 | 0.568 | 1.1226 | 0.5841 | 0.9694 | 0.7155 | 0.4309 | 0.1475 | 74 | 25 |
| Creped SB | 0.5375 | 0.6047 | 1.4204 | 0.8829 | 1.1877 | 0.8301 | 0.6502 | 0.2254 | 74 | 26 |
| Creped SB | 0.5512 | 0.5595 | 1.0153 | 0.4641 | 0.9326 | 0.6287 | 0.3814 | 0.0692 | 82 | 15 |
| Stdev | 0.0 | 0.0 | 0.2 | 0.2 | 0.1 | 0.1 | 0.1 | 0.1 | 8.7 | 10.5 |
| % CV | 3.8 | 4.4 | 13.3 | 24.7 | 9.6 | 12.7 | 20.9 | 48.9 | 11.9 | 36.3 |
| Average | 0.5 | 0.6 | 1.2 | 0.7 | 1.0 | 0.8 | 0.5 | 0.2 | 73.5 | 28.9 |
| Creped SB + 10% Reten 20LS | 0.5296 | 0.5765 | 1.2158 | 0.6862 | 0.8369 | 0.9395 | 0.3073 | 0.363 | 45 | 53 |
| Creped SB + 10% Reten 20LS | 0.5221 | 0.5538 | 1.4084 | 0.8863 | 1.0748 | 0.8749 | 0.5527 | 0.3211 | 62 | 36 |
| Creped SB + 10% Reten 20LS | 0.558 | 0.5868 | 1.2656 | 0.7076 | 0.9953 | 0.8436 | 0.4373 | 0.2568 | 62 | 36 |
| Creped SB + 10% Reten 20LS | 0.5482 | 0.5857 | 1.094 | 0.5458 | 0.9207 | 0.7474 | 0.3725 | 0.1617 | 68 | 30 |
| Creped SB + 10% Reten 20LS | 0.5486 | 0.555 | 1.5219 | 0.9733 | 0.7835 | 1.2829 | 0.2349 | 0.7279 | 24 | 75 |
| Stdev | 0.0 | 0.0 | 0.2 | 0.2 | 0.1 | 0.2 | 0.1 | 0.2 | 18.0 | 18.3 |
| % CV | 2.7 | 2.8 | 12.8 | 22.4 | 12.7 | 21.9 | 32.0 | 59.0 | 34.4 | 39.7 |
| Average | 0.5 | 0.6 | 1.3 | 0.8 | 0.9 | 0.9 | 0.4 | 0.4 | 52.3 | 46.0 |

It can be seen that when improved polarity, contact angle and micro topography are put together, this creates the better performer as shown in the above data with creped Spunbond treated with Reten 204LS. In this case the micro topography or creped spunbond by itself does not perform as well. Also, the Reten 204LS by itself performs adequately, but when the two are put together performance is even better.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article comprising:
   an outer cover;
   an absorbent core;
   a composite bodyside liner comprising a surge layer and a liquid pervious liner material defining an outer surface, wherein the outer surface of the liquid pervious liner material defines an outermost surface of the absorbent article, and where the surge layer is positioned between the liquid pervious liner material and the absorbent core, and
   a fecal adhering treatment composition applied to at least a portion of said surge layer, wherein said fecal adhering treatment composition comprises a polar component, wherein said polar component is present on said surge layer at an add-on level of at least 1% by weight of the surge layer, and wherein said fecal adhering treatment composition imparts a contact angle of fecal fluid extract of less than 90° on an outer surface of said surge layer and a surface tension of at least 20 dynes/cm on said surge layer at room temperature, wherein said surge layer is a topographical surge layer defining peaks and valleys in at least one surface of said surge layer, and wherein said fecal adhering treatment composition is applied only to said valleys defined by said topographical surge layer.

2. An absorbent article to be worn in close proximity to skin of a wearer comprising:
   an outer cover;
   an absorbent core; and
   a composite topographical bodyside liner comprising a liquid pervious liner material, a topographical surge layer, and a fecal adhering treatment composition, wherein said topographical surge layer defines peaks and valleys in at least one surface to provide topography to the composite topographical bodyside liner, wherein a fecal adhering treatment composition is applied only to said valleys of said topographical surge layer, wherein said fecal adhering treatment composition comprises a polar component configured to reduce the amount of fecal matter that remains on the skin after the absorbent article is removed from the wearer, wherein said polar component is present on said surge layer at an add-on level of at least 1% by weight of the surge layer.

3. The absorbent article as in claim 2, wherein said polar component comprises a cationic polar component.

4. The absorbent article as in claim 3, wherein said cationic polar component comprises a cationic polymer-epichlorohydrin adduct.

5. The absorbent article as in claim 2, wherein said fecal adhering treatment composition imparts a contact angle of fecal fluid extract of less than 90° on said surge layer and a surface tension of at least 20 dynes/cm on said surge layer at room temperature.

6. The absorbent article as in claim 2, wherein said liquid pervious liner material comprises a cellulosic paper sheet having an ion exchange capacity of at least 1.5 µeq/cm$^2$.

7. The absorbent article as in claim 2, wherein said liquid pervious liner material comprises a spunbond web of polypropylene fibers.

8. The absorbent article as in claim 2, wherein said liquid pervious liner material is apertured.

9. The absorbent article as in claim 2, wherein said polar component is present on said surge layer at an add-on level of at least 2% by weight of the surge layer.

10. The absorbent article as in claim 2, wherein said polar component is present on said surge layer at an add-on level of from 5% by weight to 25% by weight of the surge layer.

* * * * *